United States Patent [19]  
Chu et al.

[11] Patent Number: 4,606,824  
[45] Date of Patent: Aug. 19, 1986

[54] MODIFIED CELLULOSE SEPARATION MATRIX

[76] Inventors: Chaokang Chu, 114 Manor Cir., Hartford, Conn. 06118; Richard A. Babineau, 118 Elmwood Dr., Meriden, Conn. 06450

[21] Appl. No.: 665,402

[22] Filed: Oct. 26, 1984

[51] Int. Cl.$^4$ ............................................. B01D 15/08
[52] U.S. Cl. .................................. 210/635; 210/656; 210/767; 422/161
[58] Field of Search ...................... 210/635, 656, 198.2, 210/502.1, 505, 508, 767; 436/161

[56] References Cited

U.S. PATENT DOCUMENTS

| | | | |
|---|---|---|---|
| 2,955,067 | 10/1960 | McBurney | 210/105 |
| 3,856,681 | 12/1974 | Huber | 210/198.2 |
| 4,007,113 | 2/1977 | Ostreicher | 210/504 |
| 4,007,114 | 2/1977 | Ostreicher | 210/504 |
| 4,305,782 | 12/1981 | Ostreicher et al. | 210/505 |
| 4,309,247 | 1/1982 | Hou et al. | 210/505 |
| 4,384,957 | 5/1983 | Crowder, III et al. | 210/656 |
| 4,404,285 | 9/1985 | Hou | 436/16 |
| 4,488,969 | 12/1984 | Hou | 210/679 |
| 4,496,461 | 1/1985 | Leeke et al. | 210/198.2 |

OTHER PUBLICATIONS

Randolph, W. F., "Licensing of Limulus Amebocyte Lysate, Use as an Alternative for Rabbit Pyrogen Test," Fed. Regist., 42, 57749 (1977).

Randolph, W. F., "Human and Veterinary Drugs: Availability of Draft Guideline for Use of *Limulus Amebocyte Lysate*," Fed. Regist., 45, 3666–3669 (1980).

Jorgensen, J. H. & Smith, R. F., "Rapid Detection of Contaminated Intravenous Fluids Using the Limulus *in Vitro* Endotoxin Assay," Appl. Micro. Biol., 26, 521–524 (1973).

Novitsky, T. J. et al., "Automated LAL Testing of Parenteral Drugs in the Abott MS-2," Journ. of Parenteral Science and Technology, vol. 36, No. 1, 11–16 (1982).

Morita, T. et al., FEBS Letters, vol. 129, No. 2, pp. 318–321 (1981).

Pearson, F. C. et al., "Characterization of Limulus Amebocyte Lysate–Reactive Material from Hollow-Fiber Dialyzers," Appl. Envir. Micro., vol. 48, No. 6, 1189–1196 (1984).

Primary Examiner—John Adee  
Attorney, Agent, or Firm—Michael E. Zall

[57] ABSTRACT

A cellulose-containing separation media for effecting separation of particulate and/or molecular components from a liquid, wherein the cellulose in the separation media is essentially free of non-specific pyrogenic activity as measured by the LAL test. The separation media include filtration media and chromatographic media.

32 Claims, 11 Drawing Figures

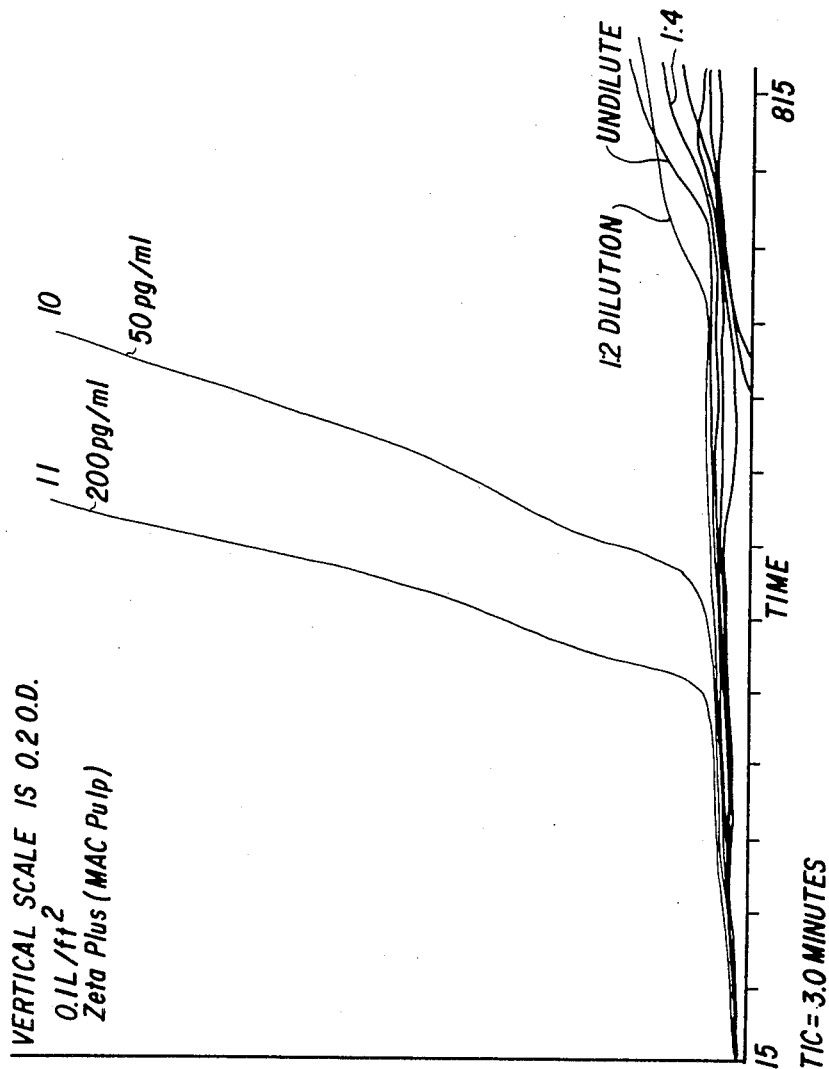

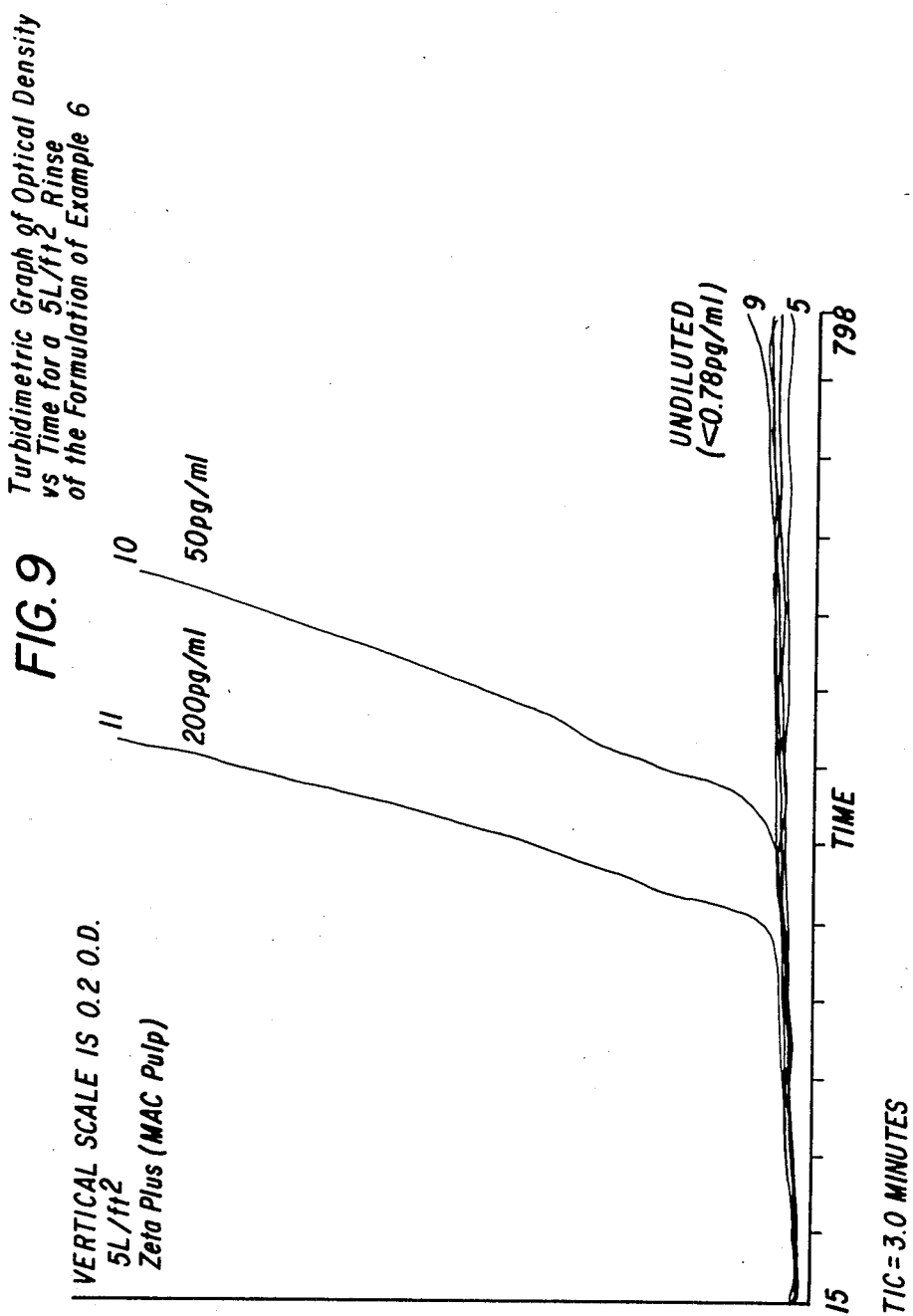

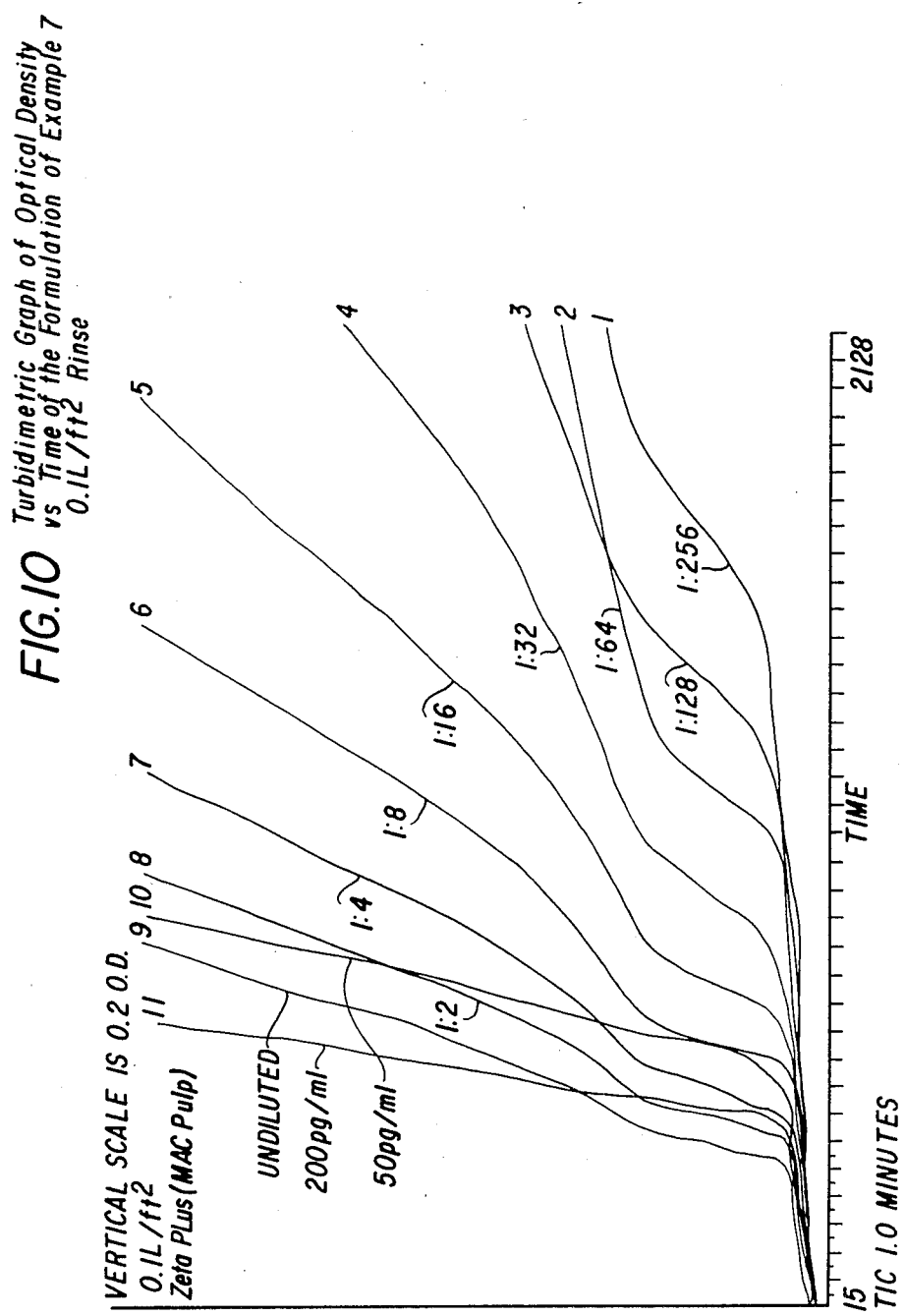

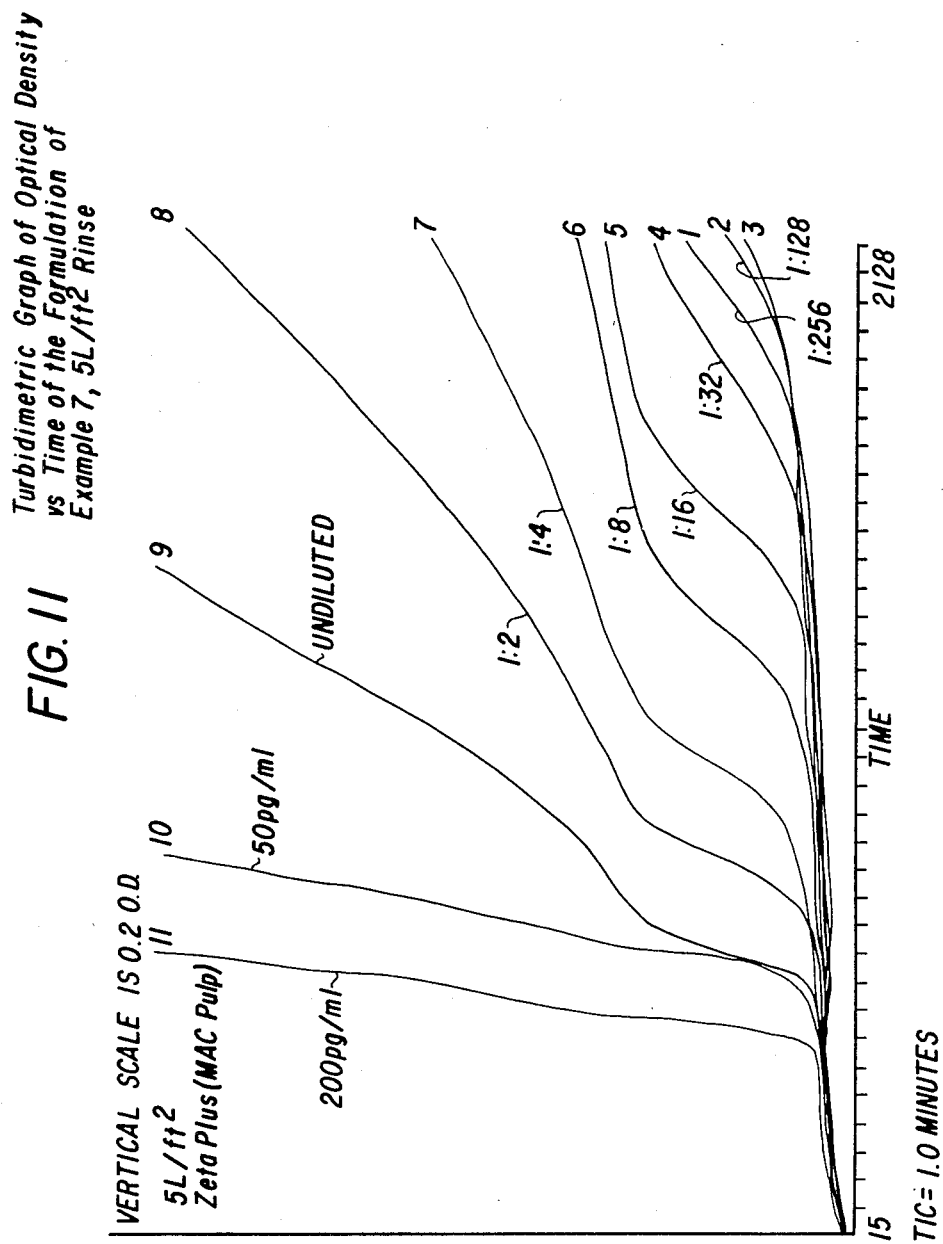

MODIFIED CELLULOSE SEPARATION MATRIX

BACKGROUND OF THE INVENTION

1. Field of the Invention

This invention is concerned with modified cellulose-containing separation media for separating particulate and/or molecular components from liquids containing same. The invention is particularly directed to separation media having utility in the pharmaceutical industry for use in the preparation and purification of pharmacologically useful liquids, i.e. parenteral solutions. Such solutions, after treatment with the separation media of this invention, are essentially free of non-specific pyrogenic reactivity.

2. Description of the Background Art

Separation of components contained in liquid may generally be divided into filtration of particulate components and separation of molecular components.

The filtration of fine particle size components from fluids has been accomplished by the use of various porous filter media through which the fluid is passed. To function as a filter, the media must allow the fluid, commonly water, through, while holding back the particulate. This holding back of the particulate is accomplished by virtue of the operation, within the porous media, of one or both of two distinctly different filtration mechanisms, namely (1) mechanical straining and (2) electrokinetic particle capture. In mechanical straining, a particle is removed by physical entrapment when it attempts to pass through a pore smaller than itself. In the case of electrokinetic capture mechanisms, the particle collides with a surface within the porous filter media and is retained on the surface by short range attractive forces.

With the exception of microporous polymeric membranes, the porous filter media known to the art as being suitable for the filtration of fine particle size particulate are typically comprised of fiber-fiber or fiber-particulate mixtures formed dynamically into sheet by vacuum felting from an aqueous slurry and then subsequently drying the finished sheet. In those fibrous filter media that depend upon mechanical straining to hold particulate, it is necessary that the pore size of the filter medium be smaller than the particle size of the particulate to be removed from the fluid. For removal of fine, submicronic particles by mechanical straining, the filter media should have correspondingly fine pores. Since the pore size of such a sheet is determined predominantly by the size and morphology of the materials used to form the sheet, it is necessary that one or more of the component materials be of a very small size, such as small diameter fibers.

As the size of the particulate sought to be removed by filtration decreases, especially into the submicron range, the difficulty and expense of providing suitably dimensioned fiber structures for optimum filtration by mechanical straining increases. Accordingly, there is considerable interest in the use of fine particulates such as diatomaceous earth in conjunction with the fibers.

However, for such materials, it is necessary to provide a matrix in order to present a coherent handleable structure for commerce and industry. Thus, at least one of the component materials in the sheet is a long, self-bonding fiber, to give the sheet sufficient structural integrity in both the wet "as formed" and in the final dried condition, to allow handling during processing, and suitability for the intended end use. Unrefined cellulose fibers such as wood pulp, cotton, cellulose acetate or rayon are commonly used. These fibers are typically relatively large, with commercially available diameters in the range of 6 to 60 micrometers. Wood pulp, most often used because of its low relative cost and fiber strength, has fiber diameters ranging from 15-25 micrometers, and fiber lengths of about 0.85 to about 6.5 mm.

Cellulose filter media sheets are conveniently formed by vacuum felting from an aqueous slurry of the component material. The vacuum felting is performed on a foraminous surface, normally a woven wire mesh which, in practice, may vary from 50 mesh to 200 mesh, with mesh openings ranging from 280 micrometers to 70 micrometers, respectively.

Assignee's U.S. Pat. No. 4,404,285 to Hou describes an embodiment wherein activated carbon in particulate form is compounded with a matrix of self-bonding cellulose fibers to form a composite sheet. The carbon particles are such that more than 90% of the particles are less than 50 microns in diameter. The composite sheet is useful for separating hormones from whole human serum.

Commonly assigned U.S. Pat. No. 4,488,969, and U.S. Ser. No. 401,361 to Hou et al., filed July 23, 1982, now U.S. Pat. No. 4,578,150, disclose a self-supporting cellulose fibrous matrix containing at least 5% by weight of fumed silica or fumed alumina. The formed silica and fumed alumina has an average particle size of less than 1 micron. The fibrous matrix is useful for delipidization and depyrogenation of fluids such as serum.

Charge modifiers have been employed to control the zeta potential of the sheet constituents and maximize performance in the electrokinetic capture of small charged contaminants. In practice, cationic charge modifiers are employed since most naturally-occurring contaminant surfaces are anionic at fluid pH of practical interest. Thus, a melamine-formaldehyde cationic colloid is disclosed for filter sheets in U.S. Pat. Nos. 4,007,113 and 4,007,114 to Ostreicher; inorganic cationic colloidal silica is disclosed in U.S. Pat. No. 4,305,782 to Ostreicher et al.; and polyamido polyamine epichlorohydrin cationic resin is disclosed in Canadian Pat. No. 1,119,105 to Hou et al. The entire disclosures of these patents are incorporated by reference herein. Such filters are sold by AMF, Inc. as ZETA PLUS.

Numerous techniques exist for the molecular separation of the components of a given sample for either analysis purposes or for product preparation purposes. One type of molecular separation embraces a variety of processes for effecting differential distribution of the sample components between two phases and such processes are generally referred to as chromatography. The differential distribution is achieved by an interchange between a moving phase, which can be a liquid or gas, and a stationary phase.

Chromatography is a general term applied to a wide variety of separation techniques based upon the sample interchange between a moving phase and a stationary phase. When gas is the moving phase (or "mobile phase" as referred to in chromatographic terminology), the technique is termed gas chromatography and when liquid is the mobile phase, the technique is termed liquid chromatography.

The collection of chromatographic techniques can be classified in several ways and the most fundamental is based on naming the types of phases used. Liquid adsorption chromatography is used extensively for organic and biochemical analysis but is limited because there are only a few suitable adsorbents. The distribution coefficient of adsorption often depends on total concentration and this behavior often results in incomplete separations. Gas-solid chromatography has generally suffered from the same defects as liquid adsorption chromatography. Ion exchange chromatography is a special field of liquid-solid chromatography and is specifically applicable to ionic species. Affinity chromatography is based on the attraction (affinity) of a ligand bonded to the solid stationary phase for a given component of the sample. Reverse phase chromatography relies on the hydrophobic characteristics of the stationary phase.

Assignee's Crowder, III, et al., U.S. Pat. No. 4,384,957, describes a column in which a mobile phase flows through a solid stationary phase; the stationary phase "system" is, broadly, a body of particulate immobilized in a porous matrix of cellulose fiber. This stationary phase has the advantage of both low pressure drop and low diffusion resistance, making it particularly suitable for commercial scale separations, particularly liquid separations. Baffle arrangements are unnecessary. As a result, it is possible to construct stable, high flow separation columns of high capacity and shorter run times which have good pressure response, freedom from channeling or fluid bypass, ease of regeneration to reproducible reuse, and the capacity to be shipped under ambient conditions or stored indefinitely. Additionally, the edges of the new stationary phase cooperate with the interior wall of the separation column to form a substantially fluid-tight seal therewith, thus preventing channeling near the walls. The entire disclosure of Crowder, III et al. is incorporated by reference herein.

The stationary phase of Crowder, III et al. comprises a porous matrix of cellulose fiber having particulate immobilized therein, wherein at least one of said fiber or particulate is effective for molecular separation. The porous matrix is substantially homogeneous with respect to each component thereof. Preferably, the particulate is effective for molecular separation. The molecular separation particulate is contained in the stationary phase at an amount effective to achieve the desired molecular separation. Among the fibers of Crowder, III et al. are cellulose fibers obtained from wood.

Assignee's U.S. application Ser. No. 576,448 to Hou et al., filed Feb. 2, 1984, a continuation-in-part of assignee's U.S. application Ser. No. 466,114, filed Feb. 14, 1983, discloses modified polysaccharide chromatographic separation media comprising polysaccharide covalently bonded to a synthetic polymer, the synthetic polymer comprising (1) a polymerizable compound which is capable of covalently coupling to the polysaccharide and (2) a polymerizable compound containing (i) an ionizable chemical gruop, (ii) a chemical group capable of being transformed into an ionizable chemical group, (iii) a chemical group capable of causing the covalent coupling of (2) to an affinity ligand or a biologically active molecule or (iv) a hydrophobic polymer. Cellulose is among the preferred modified polysaccharides.

Endotoxins, also known as bacterial pyrogens, are heat stable toxins present in bacterial cells. These materials are found primarily in gram-negative organisms and occur in the cell wall as a lipopolysaccharide (LPS) complex. These endotoxins are pyrogenic, i.e. a substance inducing fever, when injected into a mammalian species.

Biological solutions, especially those biological solutions which are intended for pharmaceutical application such as those administered by parenteral injection, must be essentially devoid of bacterial pyrogens or endotoxins. Accordingly, it is common practice in the pharmaceutical industry that biological fluids, particularly those biological fluids intended for parenteral use, be tested for pyrogen levels. One of the frequently used pyrogen level tests in the past was the rabbit pyrogen test, so called because the biological fluid in question was injected into a rabbit and the rabbit tested to determine whether fever was induced. However, this test proved to be quite cumbersome and time consuming and alternative methods of testing for pyrogens have been developed.

The use of Limulus Amebocyte Lysate (LAL) by the pharmaceutical industry has increased steadily over the last few years, both for in-process control of endotoxin contamination and for final release of medical devices in lieu of the USP pyrogen test. Guidelines for the LAL end-product use with medical devices and biological products are described by Randolph, W. F., "Licensing of Limulus Amebocyte Lysate. Use as an Alternative for Rabbit Pyrogen Test," Fed. Regist., 42, 57749 (1977). Draft guidelines have also been published for LAL use for other parenteral drugs, Randolph, W. F., "Human and Veterinary Drugs: Availability of Draft Guideline for Use of Limulus Amebocyte Lysate," Fed. Regist., 45, 3666–3669 (1980).

Traditionally, most LAL testing of pharmaceutical products has been done with the gel-clot method (Jorgensen, J. H. and Smith, R. F., "Rapid Detection of Contaminated Intravenous Fluids Using the Limulus *In Vitro* Endotoxin Assay," *Appl. Micro. Biol.* 26, 521–524 (1973)). A turbidimetric adaptation of the LAL test exists as well. The turbidimetric assay is quantitative over a continuous range of endotoxin concentrations and is often more sensitive than the gel-clot method. One such LAL turbidimetric adaptation exists for the Abbott MS-2 Microbiology System (Novitsky, T. J. et al., "Automated LAL Testing of Parenteral Drugs in the Abbott MS-2," *Journ. of Parenteral Science and Technology*, Vol. 36, No. 1, 11–16 (1982).

However, as disclosed in the Novitsky et al. article, the LAL test is subject to product-related inhibition or enhancement of the LAL test. And while Novitsky et al. is directed essentially to the development of a system for rapid characterization of parenteral drugs and for defining those factors that modify the LAL reaction in the presence of the drugs, essentially the article suggests a very real problem which exists with regard to the LAL test, namely that various non-pyrogenic substances alter the reactivity of the biological fluids being tested.

Further, applicants have now discovered that certain prior art cellulose-containing filtration media yield biological fluids which demonstrate unacceptable pyrogen levels when tested using Limulus Amebocyte Lysate. Further, the high pyrogen levels indicated by the LAL test of biological fluids which are filtrates of the cellulose-containing filtration media frequently are falsely positive, these same fluids showing only very low pyrogen levels when tested using the rabbit pyrogen test.

Accordingly, a need has continued to exist in the pharmaceutical industry for cellulose-containing separation media such as the type described in U.S. Pat. No.

4,384,957 to Crowder III et al., U.S. Ser. No. 576,448 to Hou et al., U.S. Pat. Nos. 4,007,113 and 4,007,114 to Ostreicher, U.S. Pat. No. 4,305,782 to Ostreicher et al., and Canadian Pat. No. 1,119,105 to Hou et al. discussed above, said media effective for the production and purification of biological fluids which are essentially free of non-specific pyrogenic reactivity using the LAL tests. Faced with an ever increasing demand for filtration media for use in the pharmaceutical industry, coupled with increasingly strict controls on the quality control of the finished product, coupled with the facility of pyrogen testing afforded by the LAL test, the development of cellulose-containing filtration media which produce biological fluid filtrates essentially free of non-specific pyrogenic reactivity as tested by the LAL test method are of great importance.

SUMMARY OF THE INVENTION

Assignee of the present invention is in the business of manufacturing a variety of separation media, including separation media for the preparation of biological fluids, the separation media well known and in common use in the pharmaceutical industries. Assignee recently became aware that certain biological fluids produced by the pharmaceutical industry using certain of its commercial separation media were demonstrating unsatisfactory pyrogen levels when tested utilizing the LAL tests described above. Upon investigation, it was determined that pyrogen levels of these biological fluids were, in fact, well within acceptable levels, the pyrogen levels indicated by the LAL test not coincident with pyrogen levels as demonstrated by the rabbit pyrogen test. Accordingly, the conclusion was reached that something within the separation media itself was giving a false positive when the biological fluids were tested with Limulus Amebocyte Lysate. Extensive research into the problem narrowed the field of inquiry to the cellulose in the cellulose-containing separation media.

It has now been discovered, this discovery representing the instant invention, that a cellulose-containing separation media for separating particulate and/or molecular components from a liquid is capable of providing effluent essentially free of endotoxin (pyrogen) and non-reactive as measured by the LAL test if the cellulose of the cellulose-containing separation media is a cellulose which consists of highly pure cellulose, as defined below.

Applicants have also discovered a method for producing biological fluid essentially free of non-specific pyrogenic reactivity as measured by the LAL test, the method comprising passing said biological fluid through a cellulose-containing separation media wherein the cellulose of the cellulose-containing separation media consists of highly pure cellulose, the cellulose essentially free from LAL reactive extractables.

BRIEF DESCRIPTION OF THE DRAWINGS

FIG. 8 is a turbidimetric graph of optical density vs. time for a 0.1 L/ft$^2$ rinse of the formulation of Example 6.

FIG. 9 is a turbidimetric graph of optical density vs. time for a 5 L/ft$^2$ rinse of the formulation of Example 6.

FIG. 10 is a turbidimetric graph of optical density vs. time of the formulation of Example 7, 0.1 L/ft$^2$ rinse.

FIG. 11 is a turbidimetric graph of optical density vs. time of the formulation of Example 7, 5 L/ft$^2$ rinse.

DESCRIPTION OF THE PREFERRED EMBODIMENT

Figure 1:
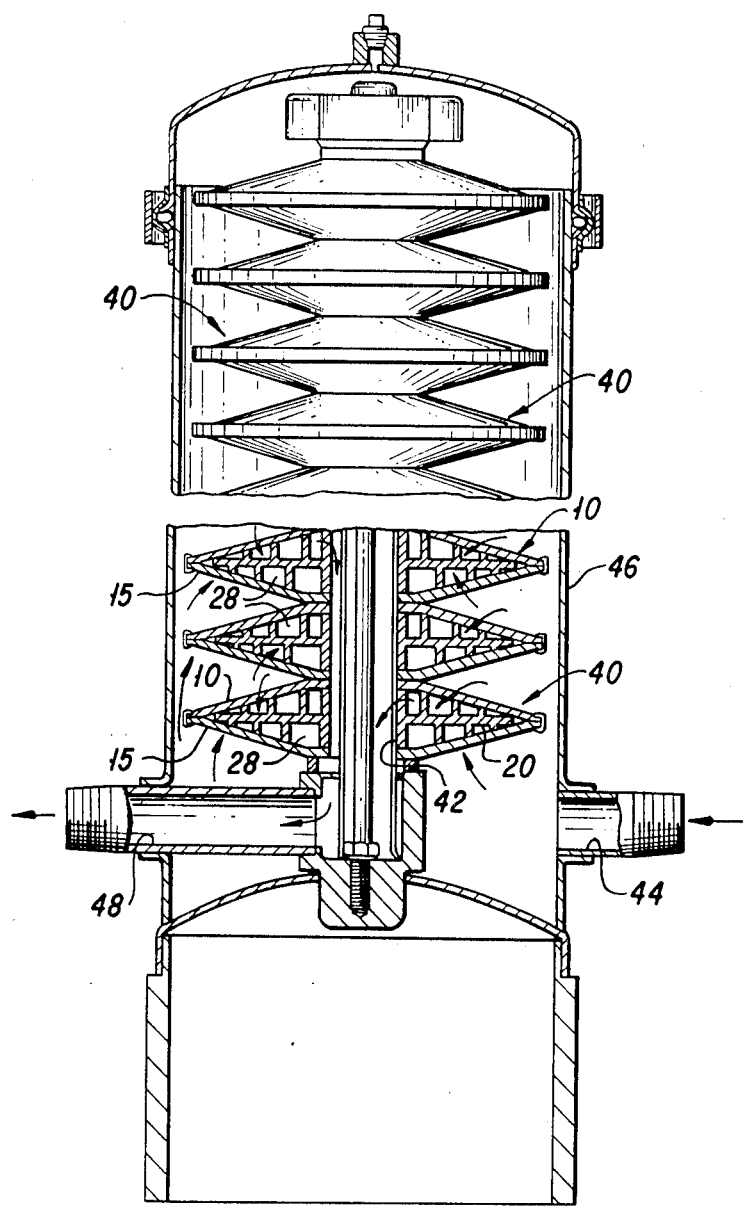
FIG. 1 is a longitudinal partial cross-sectional view of a preferred embodiment of a filter housing and filter cartridge comprised of a plurality of filter cells utilizing the filter media of this invention.

The separation media of the present invention find particular utility in the preparation of biological fluids. The term "biological fluids" or "biological liquids" as employed in the specification and claims is a liquid system which is derived from or amenable to use with living organisms, and ordinarily handled and processed under sanitary or sterile conditions, therefore requiring sanitized or sterilized media for filtration. Included are isotonic solutions for I.M. or I.V. administration, solutions designed for administration per os, as well as solutions for topical use, biological wastes or other body fluids which may comprise filterable bodies such as impurities, e.g., bacteria, viruses or pyrogens which are desirably isolated or separated for examination or disposal by immobilization or fixation upon or entrapment within separation media. The separation media of this invention are particularly suitable for production and purification from biological solutions and especially production of parenteral solutions.

The separation media in accordance with the present invention may be employed alone or in combination with other such media to treat pharmaceuticals such as antibiotics, saline solutions, dextrose solutions, vaccines, blood plasma, serums, sterile water or eye washes; beverages, such as cordials, gin, vodka, beer, scotch, whiskey, sweet and dry wines, champagne or brandy; cosmetics such as mouthwash, perfume, shampoo, hair tonic, face cream or shaving lotion; food products, such as vinegar, vegetable oils, extracts, syrups, fruit juices, make-up water or cooking oils; chemicals such as antiseptics, insecticides, photographic solutions, electroplating solutions, cleaning compounds, solvent purification and lubricating oils; and the like for retention of submicronic particles, removal of bacterial contaminants and resolution of colloidal hazes.

By the term "separation media" is intended those media useful in the separation of impurities from solution. By the term "impurities" is intended molecular and/or particulate substances dissolved in or suspended in a liquid medium, the separation of which is desired. Thus, the separation media of the present invention may be useful for producing a "purified" liquid or for the separation and obtaining of the molecular and/or particulate which is dissolved in or suspended in the liquid.

Separation media of particular interest are those separation media which effect filtration, i.e., the filter media described in U.S. Pat. No. 4,305,782 to Ostreicher et al. and separation media for effecting molecular separation, such as the chromatographic media described in U.S. Pat. No. 4,384,957 to Crowder, III et al. and Hou et al., U.S. Ser. No. 576,448, filed Feb. 2, 1984.

A. FILTRATION SEPARATION MEDIA

The preferred filter media of the present invention is comprised of an amount of particulate immobilized in a substantially porous matrix comprised of a self-bonding matrix of cellulose fibers. The preferred cellulose fibers are derived from wood pulp.

Critical to the present invention is the discovery that the use of cellulose fibers wherein the cellulose is highly purified cellulose provides a filtration media which is capable of producing filtrates demonstrating very low levels of pyrogen as tested by the LAL pyrogen test.

For the purposes of the present invention, the term "highly pure cellulose" or "highly purified cellulose" is intended to include those cellulose materials which are essentially free of non-specific pyrogenic reactivity as measured by the LAL test, and which, when tested for pyrogens using the LAL test, typically Limulus Amebocyte Lysate gel-clot test and/or Limulus Amebocyte Lysate MS-2 test, both described in full below, give pyrogen levels acceptable to the pharmaceutical industry, preferably in the range of 50 pg/ml or less. It has now been discovered, the discovery representing one aspect of the present invention, that cellulose materials which, when tested for pyrogens by the LAL test and are found acceptable, are formulated into filtration and molecular separation media, the separation media are also acceptable. Accordingly, the celluloses used in the present invention are any and all cellulose materials which, when formulated into a separation media, yield filtrates from pyrogen-free influents which are essentially free of non-specific pyrogenic reactivity.

By the term "essentially free of pyrogens" or "essentially endotoxin-free" is typically meant LAL test results demonstrating pyrogen levels of less than about 50 pg/ml, within the sensitivity of the test.

By the term "non-specific pyrogenic reactivity" is meant that the material in question, either the separation media itself or the effluent produced by the separation media, yields false positives when tested for pyrogens using the LAL tests, typically the LAL gel-clot test and/or the LAL MS-2 test.

By "false positive" is intended an indication of pyrogen where, in fact, no pyrogen is present.

By "essentially free of non-specific pyrogenic reactivity" is meant the LAL test results show less than 50 pg/ml of pyrogen reactivity.

In evaluating the separation media for non-specific pyrogenic reactivity (an indication of LAL reactivity which is elicited by a source other than pyrogen), the media (either the separation media itself or the cellulose component thereof) in its unaltered state, is subjected to a 5.0 L/ft$^2$ rinse with pyrogen-free water and then evaluated with LAL. Both the sample collection technique and the specifics of the LAL gel-clot and LAL MS-2 tests are described in full below. The first ml of pyrogen-free rinse water following the 5.0 L/ft$^2$ rinse is collected and evaluated. The cellulose materials of this invention are those cellulose materials which are sufficiently devoid of extractables, following the 5.0 L/ft$^2$ rinse with pyrogen free water, that, in the absence of pyrogens, the LAL tests show pyrogen reactivity of less than 50 pg/ml.

It has been found that among those cellulose materials used in the present invention are those highly pure cellulose materials which contain at least 90% alpha-cellulose. Cellulose exists in three forms, alpha-, beta-, and gamma-cellulose. Alpha-cellulose has the highest degree of polymerization. Beta- and gramma-cellulose have lower degrees of polymerization and are called hemi-cellulose. Extraction techniques for determining alpha-cellulose content are based on non-dilution techniques utilizing 10 and 18% sodium hydroxide. These determinations may be carried out by volumetric analysis of the filtrate or by gravametric analysis of the residue utilizing known techniques.

Suitable cellulose materials useful in the invention are commercially available from Weyerhaeuser under the commercial product name AA Sulphite, Alpha Hardwood Sulphite, and MAC Sulphite. Typical characteristics of the three commercially available cellulose materials include an alpha-cellulose content of at least 90%, AA Sulphite containing an alpha-cellulose content of 91.5%, Alpha Hardwood Sulphite containing an alpha-cellulose content of 92.0%, and MAC Sulphite containing and alpha-cellulose content of 93.0%. Whether attributable to the high alpha-cellulose content or not, these three highly pure celluloses provide excellent separation media within the scope of the present invention. These celluloses are made by the sulphite process, one such process described in Canadian Pat. No. 480,404, issued Jan. 22, 1952, and incorporated by reference herein.

Applicants believe, but do not intend to be in any way bound or limited by this belief, that the substance in the cellulose which is responsible for the false positive when production solutions are tested for pyrogens using the LAL gel-clot or MS-2 tests is 1,3-beta-D-glucan. Morita, T. et al., *FEBS Letters*, Volume 129, No. 2, pp. 318-321 (1981) suggests that transformation of coagulogen to coagulin is mediated by two independent pathways. One of the pathways is the well-recognized endotoxin-mediated pathway. The second hypothesis suggested is that 1,3-beta-D-glucan will also mediate the transformation of coagulogen to coagulin. However, Morita et al. do not in any way suggest that the 1,3-beta-D-glucans are present in cellulose or might in any way produce an artifact in biological fluids tested with the LAL-gel clot or MS-2 tests.

Applicants further believe, and again do not intend in any way to be bound by this belief, that the 1,3-beta-D-glucan exists as a component which binds the cellulose cell walls together and that the 1,3-beta-D-glucan availability is effected by the choice of pulp processing technique. The Kraft process, employing a caustic leach, is known to break down and degrade the long-chain cellulose polymers. Applicants speculated that this degradative leach, then, makes available significant quantities of the 1,3-beta-D-glucan, the now-available glucan mediating the LAL test.

Interestingly, the three commercial pulps found to be effective in the separation media of this invention are produced by the sulphite process, a process which is less severe than the Kraft process. Applicants speculate that this less severe pulp treatment makes available lower quantities of the glucan for reaction with LAL.

In order to provide a matrix which is a coherent and handleable structure for commerce and industry, it is desirable that at least one of the components that goes into forming the porous matrix is a long self-binding structural fiber. Such fiber gives the filter media, e.g.

filter sheet, sufficient structural integrity in both the wet "as formed" condition and in the final dried condition. Such a structure permits handling of the filter media during processing and at the time of its intended use. Such fibers are particularly suitable in diameters in the range of 6 to 60 micrometers. Wood pulp, for example has fiber diameters ranging from 15 to 25 micrometers, and fiber lengths of about 0.85 to about 6.5 mm.

When the amount of particulate immobilized in the porous matrix is low, i.e. less than about 50% by weight of the media, it is preferred that the porous matrix be formed of a self-bonding matrix of normal cellulose pulp having a Canadian Standard Freeness (CSF) of +400 to +800 ml.

The state of refinement of wood pulp fibers is determined by means of a "freeness" test in which measurement of the flow rate through the fibers on a standard screen is determined. Two of the most common instruments are the "Canadian Standard Freeness Tester" and the "Shopper-Riegler Freeness Tester". For a more detailed explanation of these tests, see U.S. Pat. No. 4,309,247 to Hou et al., the entire disclosure of which is incorporated herein by reference. Typical or normal wood pulps show Canadian Standard Freeness values ranging from +400 to +800 ml.

In the preferred embodiment of this invention it is desirable to have a high amount, i.e. greater than about 40% by weight of the filter media, of particulate immobilized in the porous matrix, the remainder cellulose. It is thus highly desirable to use the invention described in the aforementioned U.S. Pat. No. 4,309,247 to maintain such high content of particulate in the filter media. Broadly, a portion of cellulose pulp refined to a Canadian Standard Freeness of between about +100 and −600 ml is incorporated with a portion of the normally dimensioned cellulose pulp (+400 to +800 ml). Generally the weight ratio of unrefined to highly refined pulp will range from about 0.1:1 to about 10:1, preferably 0.2:1 to about 1:1. Such a mixture of pulps permits the retention of fine particulates up to about 80% by weight of the filter media. In any event, it is essential that the cellulose, both refined and unrefined, be a highly pure cellulose. Thus the entire cellulose content of the filtration media comprises a highly pure cellulose, the cellulose with a Canadian Standard Freeness of +400 to +800 ml and the cellulose with a Canadian Standard Freeness of +100 to −600 ml each being highly pure. The higher ratios produce medias which are more porous.

Preferably the filter media, and in particular the filter media sheet, is formed by vacuum-felting an aqueous slurry of such normal cellulose fibers, highly refined wood pulp, and particulate. This forms a filter media sheet having the particulate immobilized in a porous matrix. The filter media sheet shows a uniformly high porosity and a fine pore-sized structure with excellent filtration flow characteristics.

The amount of particulate in the filter media may be as little as 20% by weight of the filter media up to about 80% by weight. Generally, levels of about 50 to 70% by weight are employed. Various types of particulate are suitable for inclusion in the filter media of this invention. Filter aids such as activated carbon, perlite, diatomaceous earth, polymeric particulate, such as those produced by emulsion or suspension polymerization, etc. may be used. Particulate should have a specific surface area in excess of 1 square meter per gram and/or particle diameters less than about 50 microns, preferably about 3 to 50 microns. In a broad sense, any fine particulate may be suitable.

In one embodiment, at least some of the particulate material has on the average a diameter of less than one micron; i.e., a Gaussian distribution of particle diameters will have a maximum at less than one micron and is therefore termed "micro-particulate". Those sizes wherein this preferred embodiment is most useful are less than 100 millimicrons, most preferred less than 50 millimicrons, especially between 1 and 25 millimicrons. The micro-particulate is preferably fumed silica or fumed alumina. The term "fumed silica" includes materials made from the hydrolysis of $SiCl_4$ vapor in a flame of hydrogen and oxygen, and have diameters between 5 and 20 millimicrons. Fumed alumina includes aluminum oxide produced by flame hydrolysis of anhydrous aluminum chloride (e.g. Aluminum Oxide C from Degussa). This embodiment of the present invention is fully described in application Ser. No. 401,361 of Hou et al., filed July 23, 1982, now U.S. Pat. No. 4,578,150 and application Ser. No. 347,360 of Hou et al., filed Feb. 9, 1982, now U.S. Pat. No. 4,511,473. The entire disclosures of each is incorporated by reference herein. The fumed silica-containing embodiment is especially useful for delipidization of serum and for the removal of HBsAg from fluids. The fumed alumina is especially useful for removal of pyrogens from fluids.

In a different embodiment, the embodiment described in U.S. Pat. No. 4,404,285 to Hou, the entire contents of which is incorporated by reference herein, the cellulose-containing separation media contains, as at least a portion of the particulate, activated carbon particles. The carbon particles have an average diameter of less than about 50 microns. The separation media containing the activated carbon particles, as described in U.S. Pat. No. 4,404,285, are especially useful for the removal of thyroid hormones from biological materials such as serum, necessary in the preparation of zero standard serum.

In one particular embodiment, at least a portion of the particulate used to form the filter media has on its surface a divalent metal peroxide. Such an embodiment is described in commonly assigned U.S. Pat. No. 4,361,486 to Hou et al.

It is highly desirable to provide the filter media of this invention with an electropositive potential to enable the filter media to capture particulate contaminants, by not only mechanical straining, but also by electrokinetic capture of the contaminants. In filtration by mechanical straining, a particulate contaminant is removed by physical entrapment when the particle attempts to pass through a pore of smaller size. Electrokinetic capture occurs when the particle collides with the surface within the porous filter media and is retained on the surface by short range attactive forces.

Particularly preferred charge modifying agents for use in the filter media of this invention are melamine formaldehyde cationic colloid as described in U.S. Pat. Nos. 4,007,113 and 4,007,114 to Ostreicher; inorganic cationic colloidal silica, see U.S. Pat. No. 4,305,782; and polyamido polyamine epichlorohydrin cationic resin, see Canadian Pat. No. 1,119,105 to Hou et al. The entire disclosures of all of these aforementioned patents are incorporated by reference herein. A preferred charge modifying agent for use in the filter media of the present invention is the polyamido polyamine epichlorohydrin described above. A typical polyamide-epichlorohydrin-type material is that material produced by Hercules Incorporated, Wilmington, Del., having the trade name POLYCUP resin and described in Hercules Technical Bulletin OR-212A.

Other charge modifying agents may be utilized to provide an electropositive potential to the filter media, for example, cationic organic polyelectrolytes. Such polyelectrolytes are well known in the art and include those described by M. F. Hoover in "Cationic Quaternary Polyelectrolytes-A Literature Review", *J. Macromol. Sci. Chem.* A4,(6.) pp. 1327–1417, October (1970) and U.S. Pat. No. 3,354,424 to Guebert et al., the entire disclosures of which are incorporated herein by reference.

Additionally, it may be desirable to provide the filter media of this invention with an electronegative potential for entraining electropositively charge particles or repelling electronegatively charged particles, i.e. as disclosed in Greene, U.S. Pat. No. 4,282,261.

Generally, however, the specific choice of charge modifying agent depends upon factors, including cost, fluid and temperature compatability, toxicology and supplementary functional attributes such as cross linking characteristics with the porous matrix, e.g. wood pulp cellulose, in addition, to the primary filtration performance factors and intended end use. Selection of suitable charge modifying agents, from the category specified above, may be accomplished by methods well known to the art.

The amount of charge modifying agent employed is, generally, an amount which is sufficient to provide a cationic charge to the surface of the particulate and/or matrix when, for example, preparing a sheet by vacuum-felting. This will, of course, vary with the system and the modifying agents selected but can be readily determined by one skilled in the art. Thus, for a melamine formaldehyde colloid, a 5% to 10% level based upon the weight of the filter media, is found to be suitable whereas a 1% to 5% level is appropriate for a polyamide epichlorohydrin resin. In the case of inorganic cationic colloidal silica, a 4% to 8% level gives the best results.

The sequence of adding the required components to water to form the preferred cationic dispersed slurry appears to be relatively unimportant provided that the slurry is subjected to high hydrodynamic shear forces during the mixing process. Preferably the charge modifying agent, if used, is added last. Preferably, refined pulp is added to a slurry of unrefined pulp and then the particulate is incorporated. The slurry is normally prepared at a 4% consistency and then diluted with additional water to the proper consistency required for vacuum-felting sheet formation. This latter consistency value will vary depending upon the type of equipment used to form the sheet. Typically, the slurry is vacuum-formed into a sheet and oven dried in a standard manner. The preferred filter media in sheet form has a thickness of about 0.100 inches (0.25 cm) to about 0.200 inches (0.50 cm) and/or a weight of about 0.7 to 1.3 gm/sq. inch, and most preferably about 1.0 gm/sq. inch.

Figure 2:
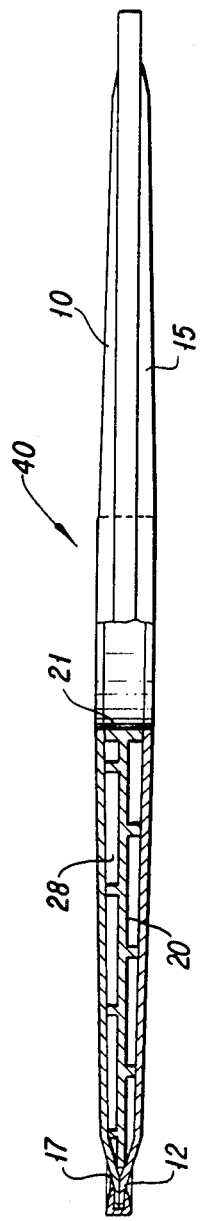
FIG. 2 is a cross-sectional view of an individual filter cell of the filter cartridge of FIG. 1.

A preferred form of utilizing the filter media of this invention is to incorporate the filter media in sheet form in a filter cell which is used to form a filter cartridge. Such filter cartridges are of the type sold by AMF Cuno under the trademark Zeta Plus. FIGS. 1 and 2 depict, respectively, such a filter cartridge and housing, and the filter cell. Referring to FIGS. 1 and 2, the filter cell (40) is comprised of two filter media (10 and 15), preferably in disc form having the flanges (12 and 17) in intimate face-to-face contact with each other, the filter media (10 and 15) and spacer means (20) all having an axial or central opening (21) of the proper size which forms a vertical conduit (42).

In operation the fluid is filtered by passing through in-take pipe (44) into a housing (46). The fluid passes from the outside of the filter cell (40) through the filter media (10 and 15) to the space (28) formed by spacer means (20). Contaminants, e.g. insolubles and microorganisms, are deposited on the outside and/or within the filter media (10 and 15) and the filtrate discharged through the discharged tube (48). Discharged tube (48) is in fluid connection with vertical conduit (42) which is in fluid connection with space (28) between the media (10 and 15).

A preferred way of producing such a filter cell is described in U.S. Pat. No. 4,347,208 to K. Southall. The entire disclosure of this patent is incorporated herein by reference.

B. MOLECULAR SEPARATION CHROMATOGRAPHIC MEDIA

The molecular separation chromatographic media of the present invention comprises a solid stationary phase which comprises a porous matrix of fiber having particulate immobilized therein, at least one of said fiber or particulate being effective for molecular separation, the matrix being substantially homogeneous with respect to each component. When used in liquid-solid flow-through molecular separations, there is a reduced pressure drop and diffusional resistance so that the columns can be used for commercial scale liquid separations in addition to analytical separations. These solid stationary phase materials of the present invention are described in greater detail in U.S. Pat. No. 4,384,957, and U.S. Ser. No. 576,448, supra, the entire disclosures of which are incorporated by reference herein.

As described in the preceding section on the filtration media, the preferred stationary phase of this invention has a porous matrix comprised of a self-bonding matrix of wood pulp fibers. The porous matrix of cellulose fibers has particulate immobilized therein, the preferred particulates including all those substances which can be provided in finely divided form and exhibit chromatographic functionality. Exemplary of such particulates are silica, alumina, diatomaceous earth, perlite, clay such as vermiculite, carbon such as activated carbon, modified polymer particulates such as ion exchange resins, crystalline cellulose, molecular sieves, and the like, the surfaces of which may be modified in conventional manner. Particle size of the particulate is not critical with 10-100 microns constituting a practical operational range. The amount of particulate may vary from 10 wt.% to up to 80 wt.% or more of the solid stationary phase. Again, one embodiment of the present invention contemplates the use of fumed silica, fumed alumina and/or activated carbon for at least a part of the particulate. The silica and alumina are described in the commonly assigned Hou et al. applications Ser. No. 347,360 and Ser. No. 401,361 described above, now U.S. Pat. Nos. 4,511,473 and 4,578,150, respectively. The carbon is described above in U.S. Pat. No. 4,404,285.

As above, when the amount of particulate immobilized in the porous matrix is low, i.e. less than about 50% by weight of the media, it is preferred that the porous matrix be formed of a self-bonding matrix of normal cellulose pulp having a CSF of +400 to +800 ml.

In the preferred embodiment, it is desirable to have a high amount of particulate, i.e. greater than about 50% by weight of the stationary phase, immobilized in the porous matrix. Again, it is desirable to use the invention described in U.S. Pat. No. 4,309,247 to Hou et al. to maintain such high content of particulate in the stationary phase. The entire disclosure of this patent is incorporated herein by reference. Broadly, a portion of cellulose pulp refined to a Canadian Standard Freeness of between about +100 and −600 ml is incorporated with a portion of the normally dimensioned cellulose pulp (+400 to +800 ml). Generally, the weight ratio of unrefined to highly refined pulp will range from about 0.1:1 to about 10:1, preferably 0.2:1 to about 1:1. Such a mixture of pulp permits the retention of fine particulates up to about 80% or more by weight of the stationary phase. However, as with the filtration media above, it is critical that the cellulose of the cellulose-containing stationary phase be highly pure cellulose, highly pure cellulose defined as above. Thus where the chromatographic media contains both refined and unrefined cellulose, each of the refined and unrefined celluloses must consist of highly pure cellulose.

The amount of particulate in the stationary phase may be as little as 10% by weight of the solid phase up to about 80% by weight. Preferably, levels of about 40% to 70% by weight are employed.

Preferably, the sheets, which form the stationary phase, are formed by vacuum-felting an aqueous slurry of unrefined cellulose fibers consisting essentially of highly pure cellulose, highly refined cellulose fibers consisting essentially of highly pure cellulose, and particulate. This forms a sheet having the particulate immobilized in a porous matrix. The sheet shows a uniformly high porosity, fine pore-size structure with excellent flow characteristics, and is substantially homogeneous with respect to the fiber and particulate. As above for the filtration media, the sequence of adding the required components to water to form the aqueous slurry appears to be relatively unimportant provided that the slurry is subjected to controlled hydrodynamic shear forces during the mixing process. The flat dimensionally stable sheet may be of any desired thickness and is cut to the appropriate dimensions for each type of column in which it is used. A column of the stationary phase can also be formed in situ, for example, by a slurry packing technique.

Figure 3:
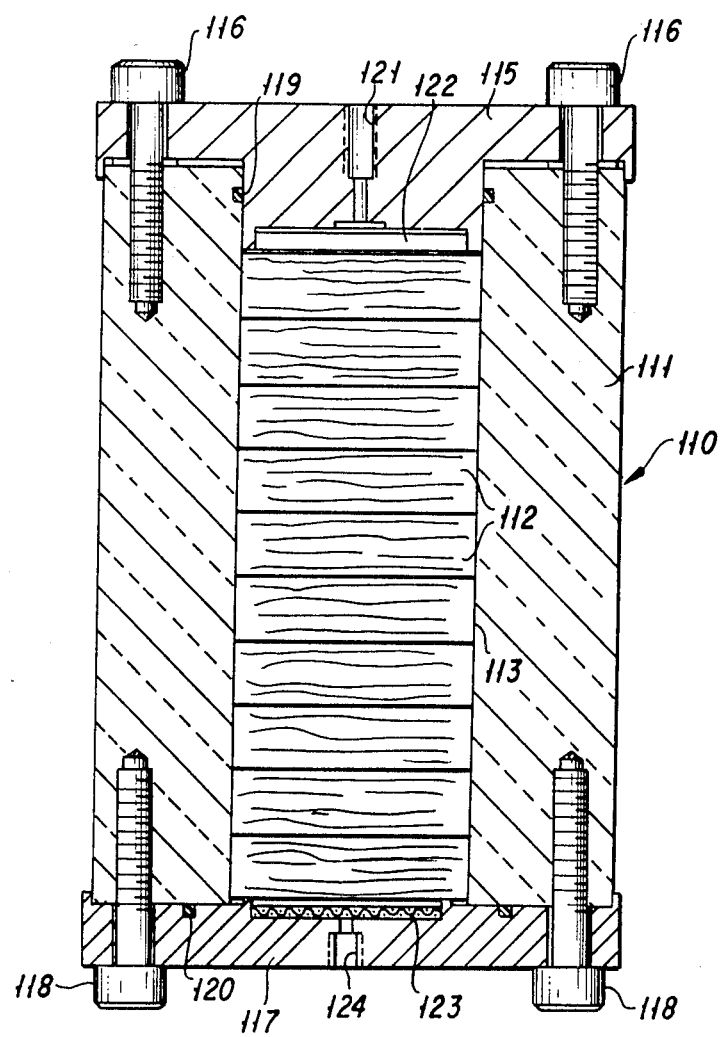
FIG. 3 is a sectional elevational view of an embodiment of a molecular separation column utilizing the chromatographic media of the present invention.

A preferred molecular separation column in accordance with the present invention comprises a plurality of elements, i.e., cut discs or pads packed into the column housing which is usually in the shape of a cylinder with a very precise internal diameter. FIG. 3 shows the preferred molecular separation column (110) for effecting differential distribution of a sample component between two phases in accordance with the present invention. The column (110) is a hollow cylinder (111) of circular cross-section which can be fabricated from any suitable material such as glass, steel, plexiglass and the like, containing a number of discs of solid stationary phase elements (112). The edges (113) of the elements (112) form a fluid-tight seal with the interior wall of the cylinder (111). The fluid-tight seal can be achieved in several ways. In one embodiment, the dimensions of the elements (112) and the interior of the cylinder (111) are such that the elements (112) are held firmly in place by a friction fit such that a pre-load compresses the elements. This requires very precise dimensional tolerances for both the interior wall of the cylinder (111) and the elements (112). The individual elements (112) are inserted in the cylinder (111) usually with some mechanical aid such as a push-rod or piston. In a preferred embodiment which is suitable when an aqueous mobile phase is being passed through the column, the elements (112) are hydrophilic and swell somewhat upon contact with the mobile phase forming the required fluid-tight seal with the interior wall of cylinder (111).

The column (110) includes an inlet cap (115) held in place by bolts (116) and an outlet cap (117) held in place with bolts (118). Inlet cap (115) is maintained in spaced relationship with cylinder (111) by spacer elements. Gasket rings (119 and 120) maintain an air-tight seal of caps (115 and 117) with cylinder (111). Inlet cap (115) is provided with an inlet orifice (121) for receiving liquid introduced into the column and inlet diffuser (122) for distributing the incoming liquid across the bore of the cylinder. Outlet cap (117) is provided with a support screen (123) to retain elements (112) within the column and outlet orifice (124) through which the separated liquid is discharged to a sample detector for analysis.

A separate embodiment of the present invention involves the modification of the invention described in commonly assigned copending application Ser. No. 576,448 to Hou et al., filed Feb. 2, 1984, a continuation-in-part of application Ser. No. 466,114, filed Feb. 14, 1983. The entire disclosure of each of these two applications is incorporated by reference herein. The invention as described generally in the two Hou et al. applications is directed to modified polysaccharide materials, including modified cellulose materials, comprising polysaccharide covalently bonded to a synthetic polymer, said synthetic polymer made from (a) a polymerizable compound which has a chemical group capable of direct or indirect covalent coupling to said polysaccharide; and (b) one or more polymerizable compounds containing (i) an ionizable chemical group, (ii) a chemical group capable of transformation to an ionizable chemical group, (iii) a chemical group capable of causing the covalent coupling of said compound (b) to an affinity ligand or a biologically active molecule, or (iv) a hydrophobic chemical group. The compositions of the said two copending applications, supra, are directed to carrier supports such as chromatographic supports.

It has now been discovered that an improvement on the chromatographic supports of the two Hou et al. applications resides wherein the modified polysaccharide material is a modified cellulosic material, said modified cellulosic material comprising a cellulose consisting essentially of high purity cellulose. Further, the invention described in the two Hou et al. applications also contemplates a fibrous chromatographic media comprising two different types of cellulose, one a modified cellulose according to the invention therein described and another an unmodified cellulose. Additionally, the modified cellulose and unmodified cellulose may further include a minor portion of cellulose pulp which has been refined to a Canadian Standard Freeness of between +100 and −600 ml. Included in the scope of the invention herein are the modified cellulosic supports wherein each of the cellulosic materials, the modified cellulose, the unmodified cellulose, and the refined cellulose, consists essentially of a highly pure cellulose, highly pure cellulose defined as above.

The modified cellulose-containing chromatographic media containing highly pure cellulose are suitable for ion-exchange chromatography, affinity chromatography, and reverse phase chromatography. In a preferred embodiment, the physical configuration of the chromatographic separation media consisting of highly pure cellulose is essentially that disclosed in commonly assigned application Ser. No. 505,532 to Leeke et al., filed June 17, 1983, now U.S. Pat. No. 4,496,461, incorporated by reference herein. As disclosed therein, the solid stationary phase comprises a swellable fibrous matrix in sheet form. Preferably, the sheet is homogeneous or substantially homogeneous, which in effect means that that stationary phase is of a uniform or substantially uniform structure and/or composition transverse or axial to the radially flowing sample.

Figure 4:
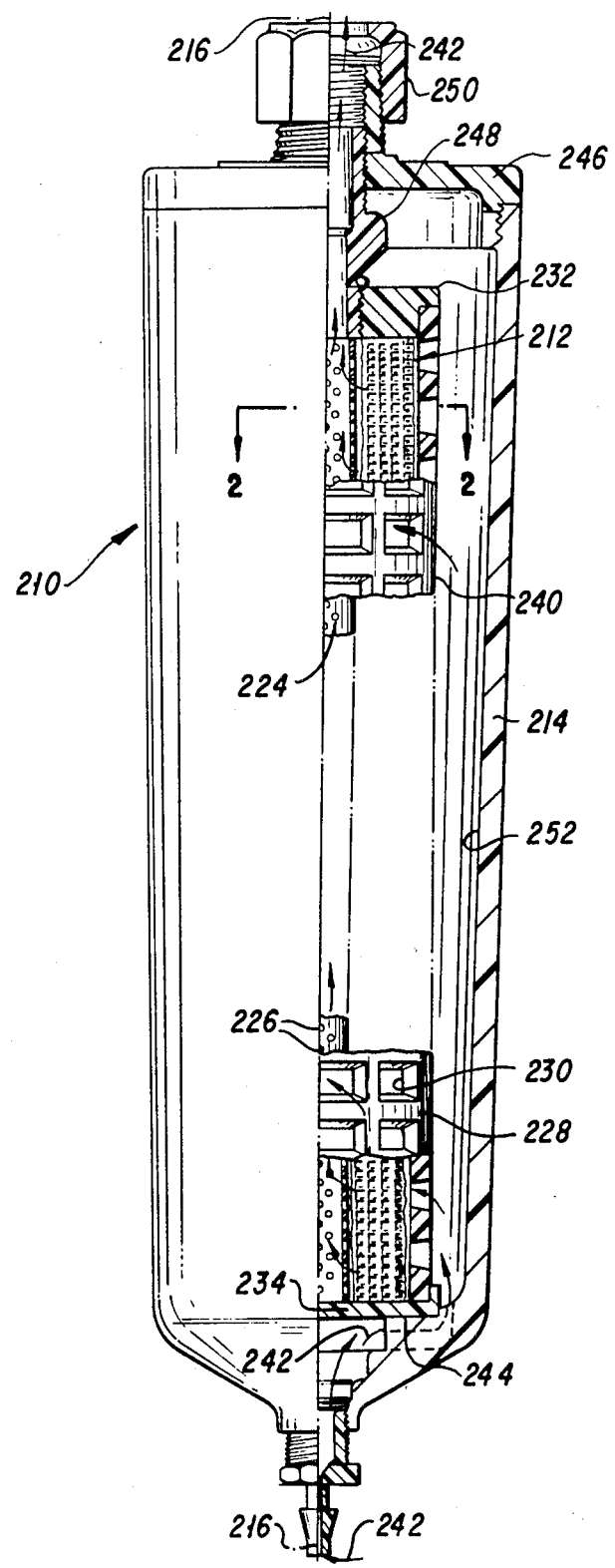
FIG. 4 is a partial sectional view of a side elevation of another preferred chromatography column using the chromatographic media of the present invention.
Figure 5:
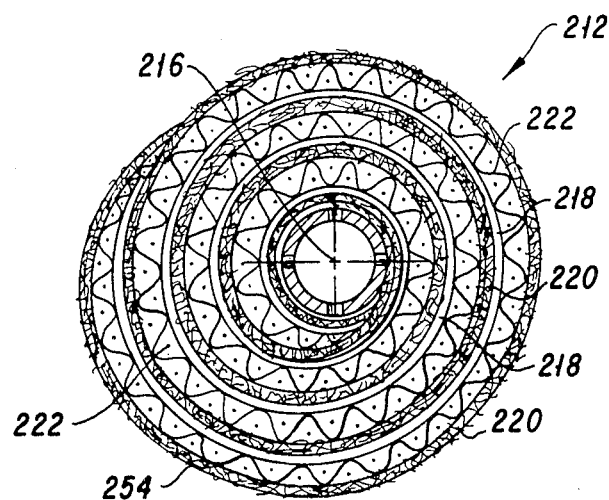
FIG. 5 is an enlarged cross-sectional view of FIG. 4, along line 2—2.
Figure 6:
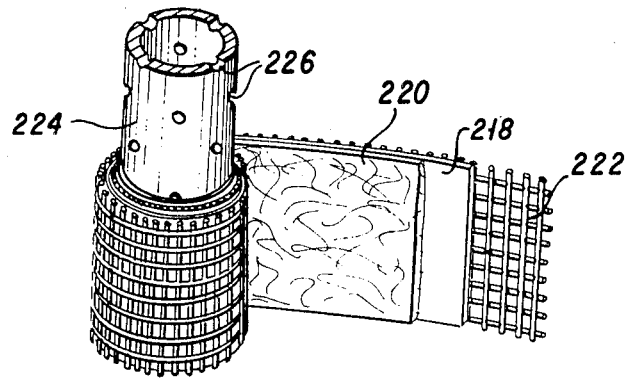
FIG. 6 is a perspective view of a portion of the solid stationary phase showing the spirally wound chromatographic media and spacer means therebetween.

Referring to the drawings, wherein like character references indicate like parts, FIGS. 4 through 6 depict a preferred embodiment of the chromatography column of this aspect of the invention. Referring to FIG. 4, the column, generally designated (210), is comprised of a cylindrical stationary phase (212), preferably in cartridge form, and a cylindrical chamber (214) which acts as a housing for stationary phase (212). The solid stationary phase (212) can be inserted into a glass, metal or polymeric tube or cylinder chamber (214) having a diameter somewhat larger than the external diameter of the stationary phase (212). Suitable fluid admission, collection and monitoring systems can also be employed with the column as in conventional analytical and preparative columns. The stationary phase (212) is positioned within the chamber (214) and preferably has a longitudinal axis (216) coaxial with the axis of the cylindrical chamber (214). Optionally, a plurality of cartridges (212) may be placed in a single housing in various configurations to effect parallel and/or series flow between the cartridges (not shown). See, for example, Assignee's copending U.S. Ser. No. 611,682, filed May 18, 1984, to Daily, et al., the entire disclosure of which is incorporated herein. The solid stationary phase has chromatographic functionality and is effective for chromatographic separation. Referring to FIGS. 5 and 6, the stationary phase (212) is constructed of a swellable fibrous matrix, usually hydrophilic swellable, in sheet form (218) which is the active media for chromatographic separation. The chromatographic media in sheet form (218) is sandwiched between a scrim layer (220) of porous wettable fabric type material of, for example, polyester woven netting, and a non-woven mesh (222). The composite sheet of chromatography media (218), layer of scrim (220) and mesh (222), preferably non-woven, is spirally wound around a foraminous cylindrical core (224) having a longitudinal axis (216), to form a plurality of layers around the axis (216). The mesh (222), due to the openness and thickness thereof, acts as a spacer means between each layer of media (218) which permits the controlled expansion of the swellable media (218) without closing off the porous structure of the media and enhances the distribution of the sample flowing through the stationary phase (212). The cylindrical core (224) is provided with apertures (226) for the flow of sample into the open interior of the core (224).

Referring to FIG. 4, the wound composite sheet, (218), (220) and (222) and core (224) are then slipped into an outer cylindrical member (228) which is also provided with apertures (230). The ends of the cylinders are then capped by end caps (232) and (234). The end caps (232) and (234) are sealed by thermoplastic fusion to the outer cylindrical member (228) and also to the ends of the composite (218), (220) and (222). The fluid or sample (242) can thus flow radially from the outside to the interior of the solid stationary phase, i.e. the open interior of core (224), since the interior and exterior are completely separated by the solid stationary phase and sealed off by end caps (232) and (234).

The preformed end caps (232) and (234) are preferably applied to the cylindrical solid stationary phase (212) by heating an inside face of the thermoplastic end cap to a temperature sufficient to soften and preferably not liquefy, a sufficient amount of the end cap to form a thermoplastic seal with the end of the cylinder (228). All of the edges of one end of the cylinder (228) are then embedded into the softened material. The softened material is then hardened, typically by ambient conditions, to form a thermoplastic sealing relationship between the sealing surface of the end caps (232) and (234), the cylinder (228) and the ends of the solid stationary phase (212) to form a leak-proof seal. Such methods of applying end caps are well known in the filtration art, see for example, assignee's PCT International Publication No. WO83/04186. Optionally, the end caps can be molded integrally in situ onto the solid stationary phase.

End caps of thermoplastic materials are preferred because of the ease of bonding, but it is also possible to use thermosetting resins in a thermoplastic, fusible or heat softenable stage of polymerization, until the bondings have been effected, after which the curing of the resin can be completed to produce a structure which can no longer be separated. Such a structure is autoclavable without danger of destroying the fluid-tight seal between the cylinder (228), the solid stationary phase (212) and the end caps (232) and (234). Thermoplastic resins having softening points sufficiently high so that they are not softened under sterilizing autoclaving conditions are preferred for biomedical use. Exemplary of the plastic materials which can be used are polyolefins.

Referring to FIG. 4, the preferred cartridge (240) has an end cap (234) on one end which does not open to the exterior of outer cylindrical member (228), but is closed off. This end cap (234) can nest on the bottom end wall (244) of cylindrical housing (214) while still permitting the flow of sample (242) into the chamber (214) around the outside of outer cylindrical chamber (228), or this lower end cap (234) of cartridge (240) is in spaced apart relationship from the bottom end wall (244) of cylindrical chamber (214), thus permitting the flow of sample (242) into the chamber (214).

The upper end of cartridge (240) has an end cap (232) which is in fluid communication with cylindrical core (224) thus permitting the flow of fluid from the center of cylindrical core (224) to the outside of end cap (232). A fitting (248) is inserted into end cap (232) so that it may engage the end wall (246) of cylindrical chamber (214). This fitting may be threaded (as shown) or separately or integrally molded with the end cap and having o-ring seals thereon. End wall (246) has thereon a threaded nipple (250) which permits the flow of treated sample (242) to pass from the core (224) through end cap (232), and end wall (246) into the process stream for additional processing. The end wall (246), and optionally end wall (244), may be threadedly attached to the wall (252) of cylindrical chamber (214) for easy access to the interior for cleaning and insertion of the cartridge (240).

PYROGEN TEST PROCEDURES

In the examples below, two types of LAL tests are employed. Immediately below, the general testing procedures are outlined. (I) below describes the sample preparation technique for the general pyrogen test of (II) or (III). The separation media is not pretreated other than a 5.0 L/ft² rinse. (II) describes a general pyrogen test procedure using the gel-clot test method for LAL analysis from Associates of Cape Cod. (III) outlines a general test procedure utilizing the Abbott MS-2 LAL test for the separation media of the present invention.

I. Sample Preparation for Pyrogen Testing of Separation Media 1.0 Purpose

To test separation media from production batches for pyrogen levels using Associates of Cape Cod clot test method.

2.0 Materials and Equipment (See FIG. 7 )
  Gelman 47 mm stainless steel filter housing (1) (Gelman 4280).
  Air line with filtered air source (2) (minimum 30 psi).
  Air pressure regulator (3).
  Ring stand with clamp to secure housing.
  Graduated cylinders: 50 ml and 100 ml (Pyrex 3022).
  Hydrogen peroxide (3%).

3.0 Sample Selection/Preparation
  3.1. Separation Media Sampling
    3.1.1 Obtain three samples representing top, middle and bottom production tank levels for quality control testing.
    3.1.2 die cut sample media into 47 mm discs.
  3.2 Preparation of Gelman Housing
    3.2.1 Remove black O-rings (4) from Gelman housing (1). Loosely assemble cap (5) and base (6) to funnel barrel (7) of housing.
    3.2.2 Wrap housing (1) in aluminum foil and depyrogenate at 250° C. for one hour.
    3.2.3 Depyrogenate O-rings (4) by soaking in 3% hydrogen peroxide for 10 minutes, followed by three rinses in non-pyrogenic water.

4.0 Procedure
  4.1 Sample Collection
    4.1.1 Assemble Gelman housing (1) with O-rings (4).
    4.1.2 Collect housing rinse control by adding 10 ml non-pyrogenic water to housing and collect effluent in depyrogenated test tube.
    4.1.3 Place separation media (8) in housing and assemble sealing media disc at Gelman base with stainless steel adapter end (9) of funnel.
    4.1.4 Pour exactly 60 ml non-pyrogenic water into Gelman housing.
    4.1.5 Attach filtered air source (2) and bring pressure up slowly using regulator (3) until a flow rate of 2 ml/min./cm sq. is achieved.
    NOTE: Flow rate=18-20 ml/min. for Gelman housing.
    4.1.6 After 49 ml of water has passed through filter, collect a 2 ml sample in a premarked 10×75 mm depyrogenated culture tube.
    NOTE: Milliliters 49-51 are an equivalent of 5 L/ft. sq. rinse.
    4.1.7 If additional media samples are to be tested, the Gelman housing must be depyrogenated between samples. Repeat entire test procedure.
  4.2 LAL Analysis
    NOTE: See procedure for LAL test methodology for Associates of Cap Cod clot test (II below) and/or Abbott MS-2 (III below) LAL testing.

II. General Pyrogen Testing Using LAL Gel-Clot Test 1.0 Purpose

The purpose of this section is to outline a general procedure for pyrogen testing of separation media using Associates of Cape Cod clot test method for LAL analysis.

2.0 Application

This procedure applies whenever LAL analysis is performed on in-process water samples and/or extract solutions of media using Associates of Cape Cod clot test method.

3.0 General
  3.1. Materials and Equipment
    Refrigerator with freezer ($-20°-+8°$ C.).
    Dry heat oven (capable of maintaining 250° C.
    Water bath or dry heat block (37° C.±1° C.).
    Vortex mixer.
    100 l pipettor with sterile disposable tips.
    100 l adjustable pipettor with sterile disposable tips.
    Aluminum foil (heavy duty).
    Parafilm.
    Kimwipes.
    Scissors.
    Clock timer (60 minutes).
    Glass marking pen.
    Test tube racks for 10×75 mm tubes and 17×150 mm tubes.
    Pipet bulb.
    5 cc sterile disposable syringe.
    Glassware:
      Disposable pipettes: 1 ml, 5 ml, 10 ml, borosilicate glass)
      17×150 mm Pyrex test tubes (borosilicate glass with Morton culture tube closures)
      10×75 mm culture tubes: B & D RTU (soda lime glass)
      250 ml Erlenmeyer flasks.
    Water: non-pyrogenic sterile water for irrigation, USP pH indicator strips or microelectrode capable of pH measurements of small liquid volumes.
  3.2 Reagents
    3.2.1 *Limulus Amebocyte Lysate* (Pyrotell 5 ml vial—50 test).
    3.2.2 *E. coli* endotoxin standard (0.5 micrograms per vial).
    3.2.3 Pyrosol reconstitution buffer.
    NOTE: All reagents purchased from Associates of Cape Cod, Inc., Woods Hole, MA 02543.

4.0 Procedure
  4.1. Preparation of Glassware
    4.1.1 17×150 mm test tubes capped with metal caps.
    4.1.2 10×75 mm RTU culture tubes wrapped in foil packs of 25 test tubes.
    4.1.3 Erlenmeyer flasks wrapped individually by covering the opening of flask with foil.
    4.1.4 Pipettes wrapped in foil packages of 25.
    NOTE: All glassware must be depyrogenated by heating at 250° C. for a minimum of one hour.
  4.2. Preparation of Limulus Amebocyte Lysate
    4.2.1 Remove frozen dried vials from freezer. Tear off the metal seal and gently remove rubber stopper (release vacuum carefully) and discard.
    4.2.2 Using a pipette, add 5 ml non-pyrogenic water or Pyrosol buffer solution to each vial. Cover with parafilm and leave at room temperature while pellet goes into solution (2 or 3 minutes). Swirl gently to mix contents.
    NOTE: Pyrotell should be used immediately after reconstitution or stored at 2°-8° C. during the working day.

NOTE: If many tests are to be performed, the contents of several vials may be pooled together.

NOTE: Lyophilized vials of LAL should be stored between −20° C. and +8° C. Reconstituted vials can be stored 24 hours at 2°–8° C.

4.3. Preparation of Endotoxin Standard 4.3.1 Remove vial from freezer and tear off metal seal.

4.3.2 Add 5 ml non-pyrogenic water via syringe and needle. Vial is sealed under vacuum so syringe should dispense automatically once needle is inserted through stopper.

4.3.3 Vortex vial continuously for 15 minutes.

4.3.4 Endotoxin stock is now ready for use. Discard rubber stopper after first use. Cover vial with parafilm and store at 2°–8° C.

NOTE: Lyophilized vial of endotoxin should be stored between −20° C. and +8° C. Reconstituted vials can be stored at 2°–8° C. for a maximum of 4 weeks.

4.4. Instructions for Using Pyrosol 4.4.1 Remove vial from refrigerator. Tear off metal seal and remove rubber stopper.

4.4.2 Withdraw 5.0 ml of the buffer solution via pipette and add to vial of Pyrotell.

4.4.3 Refer to specific instructions in 4.2 for LAL preparation.

NOTE: Pyrosol contains a phenol red pH indicator. Upon addition of Pyrosol reconstituted lysate to test samples, this indicator will: (a) remain pink in color indicating pH in proper range (pH 6–8); (b) turn yellow in color (acid); (c) turn purple in color (basic). A change in indicator color means the sample has overcome buffering capacity of Pyrosol and needs additional pH adjustment.

NOTE: Store vials of Pyrosol at 2°–8° C.

4.5 Standard Cuve & Validation of Label Claim 4.5.1 Dilute stock endotoxin (100,000 pg/ml) by preparing three ten-fold dilutions to obtain working standard containing 100 pg/ml.

4.5.2 Dilute 100 pg/ml standard by preparing two-fold dilutions to obtain standard concentrations which bracket the LAL labelled sensitivity.

4.2.3 Transfer 0.1 ml of each of the standard dilutions from 4.5.2 into 10×75 mm pyrogen-free test tubes. Test each standard in duplicate.

NOTE: Vortex each standard vigorously for 30 seconds before making transfers.

4.5.4 Transfer 0.1 ml non-pyrogenic water used for dilutions into 10×75 mm tube for negative control. Test in duplicate.

4.5.5 Add 0.1 ml lysate to each tube. Mix contents well. Incubate at 37° C.±1° C.; and read tests after 60 minutes±2 minutes.

4.5.6 The label claim is valid if a positive gel forms within ± two-fold dilution of the labelled sensitivity.

| EXAMPLE: Sensitivity = 0.125 EU/ml (12.5 pg/ml). Label claim is valid if any of the data below occurs: | | | | |
|---|---|---|---|---|
| 50 | 25 | 12.5 | 6.25 | 3.125 |
| + | + | + | + | − |
| + | + | + | − | − |
| + | + | − | − | − |

4.6 Sample Collection and Preparation 4.6.1 Collect all samples aseptically in non-pyrogenic containers and store at 2°–8° C. until tested in order to stop bacteriological activity. Do not hold samples longer than 24 hours.

4.6.2 To check pH of sample, remove a small volume with pyrogen-free pipette and test with pH indicator strips or pH electrode. pH should be between 6.0 and 7.5.

Note: All samples must be adjusted so that the pH is in optimal range (6–7.5). pH adjust all samples out of this range using sterile pyrogen-free 0.1N HCl or 0.1N NaOH, or use Pyrosol buffer solution to reconstitute Pyrotell.

4.6.3 Prepare two-fold dilution of test sample.

4.6.4 Prepare a negative control: non-pyrogenic water used for endotoxin standard dilutions and as diluent for samples.

4.6.5 Prepare a positive control: minimum concentration of endotoxin needed for gel formation.

4.6.6 Prepare a compatibility control: sample spiked with known concentration of endotoxin (not needed if sample tested is water).

4.6.7 Transfer 0.1 ml of undilute sample of each two-fold dilution and of each control into 10×75 mm pyrogen-free reaction tubes. Test all samples in duplicate.

4.6.8 Add 0.1 ml lysate to 0.1 ml sample in 10×75 mm reaction tube.

4.6.9 Agitate test tube rack with reaction test tubes gently to ensure an even dispersion of reagents. Test tubes may be vortexed gently but avoid far-mins of lysate.

4.6.10 Incubate in 37° C. water bath or dry heating block for 60 minutes±2 minutes. Do not disturb tubes during incubation period.

4.6.11 After one hour incubation, carefully remove test tubes one at a time and slowly invert 180°.

NOTE: Do not remove test tube rack from water bath. Be careful not to bump tubes against rack.

4.7 Evaluation of Results 4.7.1 Positive test indicated by formation of gel which does not collapse upon 180° inversion.

4.7.2 If negative control gels, either water, glassware or LAL is contaminated.

4.7.3 If positive control does not gel, LAL has deteriorated or test was run improperly.

4.7.4 If positive control with product does not gel, product inhibition is occurring.

4.7.5 To determine endotoxin concentration of sample, multiply labeled lysate sensitivity by the highest dilution factor at which gel formation occurs.

4.7.6 USPXX (85) Bacterial Endotoxins Test: calculations for limit test can also be used to compute results from replicate tests using the following formula:

$$(P\lambda)(f/\Sigma E)$$

P = correction factor (p=1 with solutions).
$\lambda$ = labelled lysate sensitivity (units/ml).
f = number of replicate end points.
$\Sigma E$ = sum of end point dilution factors expressed as decimal fractions.

EXAMPLES: Labelled lysate sensitive (±)=12.5 pg/ml. Given the following test data, determine the two end points by looking at the highest dilution factor at which gel formation occurs (circled (+) gels). Calculate endotoxin concentration by replacing variables in formula with appropriate values.

| Undilute | 1:2 | 1:4 | | | |
|---|---|---|---|---|---|
| | | | (A) Dilutions | | |
| + | + | − | (1) | $\dfrac{(12.5 \text{ pg/ml}) (2)}{(0.5 + 0.5)}$ | = 25 pg/ml |
| + | + | − | | | |
| | | | (B) Dilutions | | |
| + | + | + | (1) | $\dfrac{(12.5 \text{ pg/ml}) (2)}{(0.5 + 0.5)}$ | = 33 pg/ml |
| + | + | − | | | |

III. Abbott MS-2 LAL Testing 1.0 Purpose

To outline a test procedure for pyrogen testing of separation media using the Abbott MS-2 Research System.

2.0 Application

This procedure applies whenever a highly sensitive or more quantitative method of LAL testing than the gel-clot test is needed to perform testing of water samples and/or extract solutions of media.

3.0 General 3.1 Materials and Equipment

Refrigerator with freezer (−20° C.−+8° C.)
Dry heat oven (capable of maintaining 250° C.)
Vortex mixer
Aluminum foil (heavy duty)
Parafilm
Scissors
Digital timer (accuracy in seconds)
Glass marking pen
Test tube rack for 17×150 mm test tubes.
5 cc sterile disposable syringe (B-D)
Sterile hypodermic needle B-D 180-1½
Tridak Stepper Repetitive Pipettor (calibrated to deliver 0.2 ml)
Glassware:
　Disposable pipettes: 1 ml, 5 ml, 10 ml (borosilicate glass)
　17×150 mm Pyrex test tubes with Morton culture tube closures
　250 ml Erlenmeyer flasks
　Ampvettes (Abbott)
Ross pH Electrode
Ampvette cartridge adapter (Abbott)
LAL agitator
Abbott MS-2 Research System
Water: Non-pyrogenic sterile water for irrigation USP.

3.2 Reagents 3.2.1 MS-2 formulated Limulus Amebocyte Lysate (5 ml vial).

3.2.2 *E. coli* endotoxin standard (0.5 micrograms per vial).

NOTE: All reagents purchased from Associates of Cape Cod, Woods Hole, MA 02543

4.0 Procedure 4.1 Preparation of Glassware 4.1.1 17×150 mm test tubes capped with metal caps.
4.1.2 Ampvettes wrapped in foil packs of 11.
4.1.3 Pipettes wrapped in foil packages of 25.
4.1.4 Erlenmeyer flasks wrapped individually by covering the opening of flask with foil.

NOTE: All glassware must be depyrogenated by heating at 250° C. for a minimum of 1 hour.

4.2 Preparation of Limulus Amebocyte Lysate 4.2.1 Remove frozen dried vials from freezer. Tear off metal seal and gently remove rubber stopper (release vacuum carefully) and discard.

4.2.2 Use a pipette, add 5 ml non-pyrogenic water to each vial. Cover with parafilm and leave at room temperature while pellet goes into solution. Swirl gently to mix contents.

NOTE: Lyophilized vials of LAL should be stored between −20° C. and +8° C. Reconstituted vials can be stored 24 hours at 2°–8° C.

4.3 Preparation of Endotoxin Standard 4.3.1 Remove vial from freezer and tear off metal seal.

4.3.2 Add 5 ml non-pyrogenic water via syringe and needle. Vial is sealed under vacuum so syringe should dispense automatically once needle is inserted through stopper.

4.3.3 Vortex vial continuously for 15 minutes.

4.3.4 Endotoxin stock is now ready for use. Discard rubber stopper after first use. Cover vial with parafilm and store at 2°–8° C.

NOTE: Lyophilized vial of endotoxin should be stored −20° C. to +8° C.

Reconstituted vials can be stored at 2°–8° C. for a maximum of 4 weeks.

4.4 LAL Test Method 4.4.1 Open MS-2 ampvette cartridge and fill the 11 positions with pyrogen-free ampvettes. Check each ampvette for cracks, holes or irregularities in glass and discard damaged ampvettes.

4.4.2 Prepare standard reference curve by diluting stock endotoxin (100,00 pg/ml) to 1600 pg/ml and then diluting by serial two-fold dilutions down to 0.2 pg/ml.

4.4.3 Prepare serial two-fold dilutions of test sample.

4.4.4 Pipette 0.8 ml undiluted test sample or sample dilution into ampvettes in cartridge positions 1 through 9. Addition should be from least to greatest concentration.

4.4.5 Pipette 0.8 ml 50 pg/ml endotoxin standard into ampvette in cartridge position 10.

4.5.6 Pipette 0.8 ml 200 pg/ml endotoxin standard into ampvette in cartridge position 11.

4.5.7 Fill 5 cc sterile syringe and needle assembly with reconstituted MS-2 lysate.

4.5.8 Insert lysate-filled syringe into precalibrated Tridak repetitive pipettor and dispense 0.2 ml lysate into each ampvette. Addition should be from position 1 to position 11.

4.5.9 Cover openings of ampvettes with a strip of parafilm and close lid of ampvette cartridge.

4.5.10 Insert ampvette cartridge into automatic LAL agitator and allow contents to mix for 1 minute.

4.5.11 Insert ampvette cartridge into MS-2 analysis module and allow to equilibrate for 3 minutes.

4.5.12 After 3-minute equilibration time, instruct MS-2 command module to begin recording optical density at 30 second intervals.

4.6 Data Evaluation 4.6.1 At the conclusion of the test, determine onset time of each test sample or dilution and compare to that of the 50 and 200 pg/ml reference standards, generating a delta time.

4.6.2 Using the delta time for each sample, extrapolate from the standard reference curve (1600 pg/ml–0.2 pg/ml) and determine endotoxin concentration for the unknown sample.

Having now generally described the invention, a better understanding may be had by reference to the following examples, none of which are intended to be limiting unless otherwise specified.

EXAMPLE 1 (Comparative Example)

Kamloops Kraft (kamloops), commercially available wood-derived cellulose from Weyerhaeuser was slurried in water and vacuum-felted to form a sheet of porous filtration media.

Figure 7:
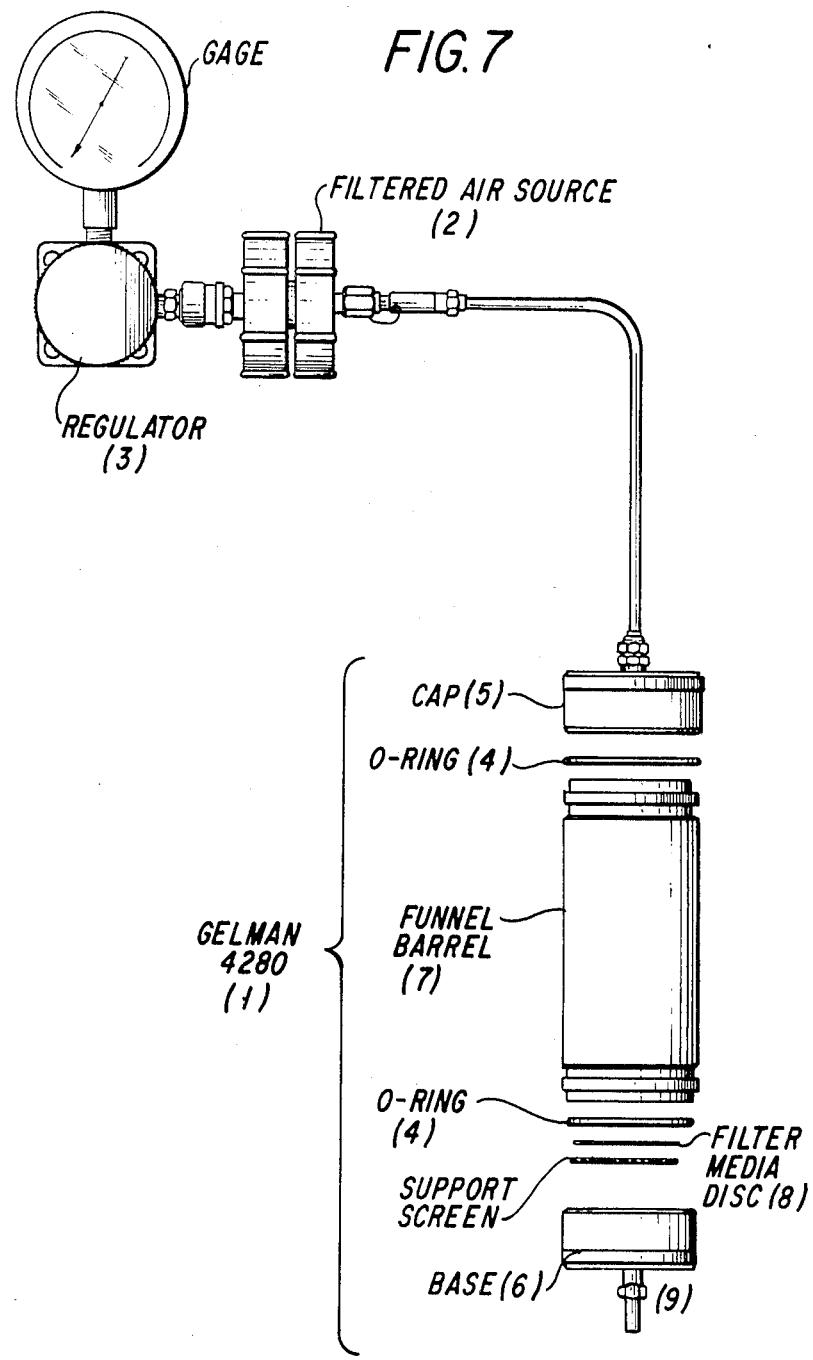
FIG. 7 is a diagrammatic representation of the apparatus for sample preparation in LAL testing.

47 mm discs (5) were cut from the sheet and placed in a cartridge as shown in FIG. 7.

Using the collection procedure set out in (I) above, each of the five discs, separately, was rinsed and the first ml following a 5 L/ft² rinse collected. The five samples were pooled and evaluated for pyrogens using the MS-2 system for LAL reactivity as set out in III above.

The results are shown in Table 1.

TABLE 1

A. Sample Collection

| Kamloops 5L/ft² | Pressure (psig) | Flow Rate (mls/min) |
| --- | --- | --- |
| 47 mm disc 1 | 1.0 | 23.2 |
| 47 mm disc 2 | 1.5 | 26.0 |
| 47 mm disc 3 | 1.0 | 21.3 |
| 47 mm disc 4 | 1.5 | 28.8 |
| 47 mm disc 5 | 2.0 | 31.6 |

B. Pyrogen Levels

| Sample | Dilution | Endotoxin Concentration | Final Concentration (pg/ml) (conc. × dilution factor) |
| --- | --- | --- | --- |
| Kamloops 5L/ft² extract | Undiluted | >1600 | >1600 |
| | 1:2 | 942.6 | 1885 |
| | 1:4 | 309.0 | 1236 |
| | 1:8 | 111.0 | 888 |
| | 1:16 | 45.6 | 729.6 |
| | 1:32 | 12.0 | 384 |
| | 1:64 | 5.6 | 358.4 |
| | 1:128 | 1.1 | 140.8 |

As may be seen from Table 1, kamloops cellulose is highly LAL reactive, indicating high pyrogen levels in the tested sample, the undiluted sample showing a pyrogen level of 1600 pg/ml. Further, if the test were reflective of endotoxin presence, column 3 (concentration×dilution factor) should be constant within experimental error. The substantial variations from a constant indicates the presence of extractables which yield a false endotoxin response (non-specific LAL reactivity).

EXAMPLE 2

Several cellulose materials obtained from Weyerhaeuser were evaluated as possible material sources for the preparation of filtration media.

Using the procedure set out in Example 1 above, four different materials were tested. Sample 1 was MAC$^R$ pulp; Sample 2 was AHDWD$^R$ pulp; Sample 3 was AA$^R$ pulp; and Sample 4 was kamloops pulp. Samples 1-3 are high purity cellulose.

As in Example 1, five discs of each sample were rinsed with 5 L/ft² of water and the first subsequent ml collected, pooled, and evaluated for LAL reactivity using the Abbott MS-2 system for LAL reactivity described in III above. The results are reported in Table 2 below.

As may be seen from Table 2, the high purity cellulose (Samples 1-3) exhibited a very low LAL reactivity. Further, any non-specific LAL reactivity was overcome at a 4:1 dilution. None of Samples 1-3 responded with the extreme non-specific LAL reactivity demonstrated by the kamloops cellulose (Sample No. 4), indicating the presence of extractable artifacts, possibly 1,3-beta-D-glucans.

TABLE 2

A. Sample Collection

| Sample (No.) | | Pressure Flow (psig) | Flow Rate (mls/min) |
| --- | --- | --- | --- |
| MAC pulp (1) | 47 mm disc 1 | 0.5 | 21.3 |
| | 47 mm disc 2 | 0.5 | 20.5 |
| | 47 mm disc 3 | 0.5 | 21.0 |
| | 47 mm disc 4 | 0.5 | 31.5 |
| | 47 mm disc 5 | 0.5 | 30.5 |
| AHDWD pulp (2) | 47 mm disc 1 | 0.5 | 14.7 |
| | 47 mm disc 2 | 0.5 | 24.5 |
| | 47 mm disc 3 | 0.5 | 20.2 |
| | 47 mm disc 4 | 0.75 | 21.6 |
| | 47 mm disc 5 | 1.0 | 29.3 |
| AA pulp (3) | 47 mm disc 1 | 0.5 | 30.9 |
| | 47 mm disc 2 | 0.5 | 19.0 |
| | 47 mm disc 3 | 0.5 | 16.4 |
| | 47 mm disc 4 | 0.5 | 19.4 |
| | 47 mm disc 5 | 0.5 | 21.1 |
| Kamloops (4) | 47 mm disc 1 | 1.0 | 23.2 |
| | 47 mm disc 2 | 1.5 | 26.0 |
| | 47 mm disc 3 | 0 | 21.3 |
| | 47 mm disc 4 | 1.5 | 28.8 |
| | 47 mm disc 5 | 2.0 | 31.6 |

B. Pyrogen Levels

| Sample | Dilution | Endotoxin Concentration | Final Concentration (pg/ml) (conc × dilution factor) |
| --- | --- | --- | --- |
| MAC pulp 5L/ft² extract (1) | undiluted | 9.1 | 9.1 |
| | 1:2 | 2.9 | 5.8 |
| | 1:4 | 1.4 | 5.6 |
| | 1:8 | 0.46 | 3.7 |
| | (1:16–1:128 <0.2) | | |
| AHDWD₂ pulp 5L/ft² extract (2) | undiluted | 14.3 | 14.3 |
| | 1:2 | 4.5 | 9.0 |
| | 1:4 | 1.9 | 7.6 |
| | 1:8 | 0.8 | 6.4 |
| | 1:16 | 0.43 | 6.88 |
| | (1:32–1:128 <0.2) | | |
| AA pulp 5L/ft² extract (3) | Undiluted | 17.0 | 17.0 |
| | 1:2 | 5.0 | 10.0 |
| | 1:4 | 1.7 | 6.8 |
| | 1:8 | 0.94 | 7.52 |
| | 1:16 | 0.44 | 7.04 |
| | 1:32 | 0.24 | 7.68 |
| | (1:64–1:128 <0.2) | | |
| Kamloops 5L/ft² extract (4) | Undiluted | >1600 | >1600* |
| | 1:2 | 942.6 | 1885.2 |
| | 1:4 | 308.8 | 1235.2 |
| | 1:8 | 111.0 | 888.0 |
| | 1:16 | 45.6 | 729.6 |
| | 1:32 | 12.0 | 384.0 |
| | 1:64 | 5.6 | 358.4 |
| | 1:128 | 1.1 | 140.8 |

*Non-specific LAL reactivity

EXAMPLE 3

Several cellulose media were evaluated for quantitative pyrogen using the gel-clot test set out in II above and the MS-2 test set out in III above.

The LAL reagent used was Pyrotell from Associates of Cape Cod, Inc., having a sensitivity of 0.15 EU/ml. The test procedure followed was that described in the Pyrotell instruction booklet. Samples were initially diluted 1:1 (undiluted), 1:2, 1:4, and 1:8. If those dilutions failed to produce satisfactory end points, then further dilutions were tested. The results listed in Table 3 give endotoxin concentration of the sample's supernatant. As may be seen therein, of the 12 cellulose materials evaluated, only three (AHDWD, AA, and MAC)

showed endotoxin levels below 50 pg/ml. There was good correlation between MS-2 and gel-clot LAL tests.

TABLE 3

| Sample | Supplier | Gel-Clot (ACC) pg/ml | MS-2 pg/ml |
|---|---|---|---|
| AHDWD Pulp | Weyerhaeuser | 30 | 14.3 |
| MAC Pulp | Weyerhaeuser | 30 | 9.05 |
| AA Pulp | Weyerhaeuser | 30 | 17.0 |
| Viscokraft Pulp | Intern'l Paper | 90 | N.D. |
| Acetakraft Pulp | Intern'l Paper | 150 | N.D. |
| Q-90 Pulp | Domtar | 600 | N.D. |
| Bahiacel Sisal Pulp | Domtar | 1500 | N.D. |
| Kamloop Pulp | Weyerhaeuser | 600 | 1600 |
| R.P. −250 CSF | | 3000 | N.D. |
| R.P. −100 CSF | | 3000 | N.D. |
| R.P. +5 CSF | | 2200 | N.D. |

NOTES: N.D. = Not Done
R.P. = Refined Kamloop Pulp, the refining performed at Assignee's facility in Stafford Springs

EXAMPLE 4

Several different Zeta Plus media, in cartridge form, obtained from AMF, Inc., Meriden, Conn., and representing commercial technology existing prior to this invention, were evaluated for LAL reactivity. The cartridges, having an eleven square foot surface area, were flushed with 55 liters of non-pyrogenic water, the equivalent of a 5.0 L/ft$^2$ rinse as above. The first subsequent filtrate was then collected and samples prepared for LAL testing. The results are reported in Table 4 below. As may be seen from Table 4, all cartirdge effluent demonstrated non-specific pyrogenic reactivity with the LAL testing.

TABLE 4

| Sample | Supplier | Gel-Clot (ACC) pg/ml | MS-2 pg/ml |
|---|---|---|---|
| 90SP lot 8131 (−250 R.P.) | AMF, Inc. | 60 | N.D. |
| 90SP lot 9062 (−250 R.P.) | AMF, Inc. | 12.5 | 331 |
| 90SP lot 9249 (−250 R.P.) | AMF, Inc. | 120 | N.D. |
| 90SP lot 9290 (−250 R.P.) | AMF, Inc. | 70 | N.D. |
| 90SP lot 9296 (−250 R.P.) | AMF, Inc. | 140 | N.D. |
| 90SP lot 9297 (−250 R.P.) | AMF, Inc. | 120 | 214 |
| 90SP lot 9298 (−250 R.P.) | AMF, Inc. | 120 | 256 |
| 90SP lot 9436 (0 R.P.) | AMF, Inc. | 12.5 | 85 |

NOTES: N.D. = Not Done
90SP = Zeta Plus Cartridges from AMF, Inc.

Example 5

Several cellulose media were evaluated for quantitative pyrogen using the gel-clot test set out in II above and the MS-2 test set out in III above.

The effects of four different rinse-up solutions on the media were evaluated. The four different rinse-out solutions evaluated were (1) cold deionized water; (2) hot (50° C.) tap water; (3) 8% citric acid; (4) 20% aqueous ethanol.

Five 8" cartridges made with Zeta Plus media from AMF, Inc., Lot No. 9082, were used to test the effect of rinse-out on media LAL reactivity. The media were as in Example 4 above. The first cartridge was sampled unrinsed, the other four were rinsed with cold (23° C.) D.I. water, hot (50° C.) water obtained directly from the pilot plant water heater, 8% citric acid, and 20% ethyl alcohol, respectively. Cartridges were rinsed in a Cuno 8" Zeta Plus housing at a flow rate of 500 cc/min, 1–2 psi. Neither the housing nor the tubing used were depyrogenated. After one hour of rinsing, strips of media were cut from the cartridge. These strips were dried for 24 hours at 65° C, then sliced up and soaked for LAL testing.

Each media sample to be tested was first sliced into thin short strips. Two 100 g portions of these media strips were then weighted into separate depyrogenated 100 ml beakers. Approximately 25 g of sterile water was added to each beaker. The beakers were covered with Parafilm and then placed in the refrigerator for approximately 16 hours. After 16 hours of soaking, the beakers were shaken to thoroughly suspend the sample slurry. About 2.5 ml of slurry from each beaker was transferred to a depyrogenated 10×75 sample tube. The tubes were centrifuged at 1,000 rpm for 10 minutes to precipitate suspended media fibers. The supernatants were diluted for LAL testing.

The LAL reagent used was Pyrotell from Associates of Cap Cod, Inc., having a sensitivity of 0.15 EU/ml. The test procedure followed was that described in the Pyrotell instruction booklet. Samples were initially diluted 1:1 (undiluted), 1:2, 1:4, and 1:8. If those dilutions failed to produce satisfactory end points, then further dilutions were tested. The results listed in Table 5 give endotoxin concentration of the sample's supernatant, and each value represents the average of two beakers. As may be seen from Table 5, rinsing with the various solutions did not produce a satisfactory endotoxin value, indicating non-specific pyrogenic reactivity.

TABLE 5

| Sample | Supplier | Gel-Clot (ACC) pg/ml | MS-2 pg/ml |
|---|---|---|---|
| 90SP Before Rinse Up | AMF, Inc. | 300 | N.D. |
| 90SP After Cold D.I. Water | AMF, Inc. | 340 | N.D. |
| 90SP After Hot Tap Water | AMF, Inc. | 120 | N.D. |
| 90SP After 8% Citric Acid | AMF, Inc. | 1350 | N.D. |
| 90SP After 20% Ethanol | AMF, Inc. | 120 | N.D. |

NOTES: N.D. = Not Done
90SP = Zeta Plus Media

EXAMPLE 6

An experimental sheet filter material was formulated to evaluate its LAL reactivity. The filter material was formulated from the following constituents:

| | |
|---|---|
| MAC pulp | 16.6% |
| Refined MAC pulp (−250 CFS) | 21.9% |
| Diatomaceous Earth (D.E. 215)[1] | 30.7% |
| Perlite (Perlit 416)[2] | 30.7% |
| Resin 1884[3] | 1.98% |
| (Based on weight of pulp, refined pulp, perlite and diatomaceous earth) | |

[1]D.E. 215 Grefco, Dicalite Div., Los Angeles, CA
[2]Perlite 416 Grefco, Dicalite Div., Los Angeles, CA
[3]Resin Dicup 1884 Hercules, Inc., Wilmington, DE The slurry of components was mixed as an aqueous slurry and vacuum felted in the conventional manner, using the procedure as described in U.S. Pat. No.

4,309,287 to Hou et al., substituting the highly pure cellulose (MAC pulp from Weyerhauser).

Three 47 mm discs were cut from the thus-formed sheet and rinse samples prepared in accordance with the procedure set out in II above. Samples from each of the three discs were pooled and evaluated for pyrogens using both of the above-described LAL reactivity tests, the MS-2 test (III) and the gel-clot test (II).

The data from each of the tests is reported below at Table 6. Additionally, the turbidimetric graphs are shown at FIGS. 8 (0.1 L/ft² rinse) and 9 (5 L/ft² rinse). On FIGS. 8 and 9, the ordinate of the Cartesian coordinates represents the optical density, while the abscissa of the Cartesian coordinates represents time.

TABLE 6

A. Sample Collection

| | Pressure Flowed AT (psig) | Flow Rate At Collection (mls/min) |
|---|---|---|
| Experimental sheet (MAC pulp) | | |
| 47 mm disc 1 | 5.0 | 18.9 |
| 47 mm disc 2 | 7.5 | 29.3 |
| 47 mm disc 3 | 6.5 | 24.9 |

B. Pyrogenicity
1. MS-2 Test

| Sample | Dilution | Endotoxin Concentration | Final Concentration (pg/ml) (conc. × dil'n factor) |
|---|---|---|---|
| 0.1 L/ft² (pH 6.89) | undiluted | inhibitory - not able to be calculated | |
| | 1:2 | *5.68 | 11.4 |
| | 1:4 | <0.78 | — |
| 5 L/ft² (pH 6.72) | undiluted | <0.78 | — |
| | 1:2 | <0.78 | — |
| | 1:4 | <0.78 | — |
| R.O. Water | undiluted | 206 | 206 |

2. Gel Clot Test

| 0.1 L/ft² | 12.5 pg/ml (end point at undiluted) |
| 5 L/ft² | <12.5 pg/ml (no end point) |

*Non-specific reactivity overcome at 1:2 dilution

As may be seen from the LAL tests, the filter material formed from the purified cellulose is very non-reactive, showing pyrogen levels of less than 12.5 pg/ml after the equivalent of a 5L/ft² rinse. This is particularly noteworthy in view of the pygrogen levels found in the R.O. water (reverse osmosis water) itself.

It was also discovered that the formulations were very sensitive to bacterial contamination of both the processing equipment and the testing equipment. Slurry formulations left overnight in the slurry tank prior to sheet formulation gave spurious results. Also, non-depyrogenated test equipment could also give false indication of high pyrogen levels.

EXAMPLE 7

A second formulation was prepared in accordance with Example 6, the components as follows:

| MAC Pulp (unrefined) | 8.0% |
| Refined MAC pulp (−441 CSF) | 22.0% |
| Perlite (Perlite 416) | 35% |
| Diatomaceous Earth (D.E. 215) | 35% |
| Resin Dicup 1884 | 2.25% (based on total weight of other components) |

Samples were prepared and evaluated as in Example 6, the results reported in Table 6 below. Additionally, FIGS. 10 and 11 are Turbidimetric Graphs of the MS-2 evaluation.

TABLE 7

| Test Data | Flow rate of rinse out - 2.0 ml/min/cm² |
|---|---|
| | Test Pressure = 7.0-8.0 psi |
| Sample pH | 0.1 L/ft² rinse = 6.45 |
| | 5.0 L/ft² rinse = 7.00 |
| A.C.C. Clot Test | 0.1 L/ft² = 25 pg/ml |
| | 5.0 L/ft² = 12.5 pg/ml |

MS-2 Test Results

| Sample | Dilution | Endotoxin (pg/ml) in Sample Dilution | Total Endotoxin (pg/ml) in Sample (× dil'n factor) |
|---|---|---|---|
| MAC Pulp 0.1 L/ft² rinse | Undiluted | 1048.88 | 1048.88 |
| | 1:2 | 420.17 | 840.34 |
| | 1:4 | 133.41 | 533.64 |
| | 1:8 | 46.43 | 371.44 |
| | 1:16 | 12.78 | 204.48 |
| | 1:32 | 2.60 | 83.20 |
| | 1:64 | 0.64 | 40.96 |
| | 1:128 | 0.30 | 38.40 |
| | 1:256 | 0.12 | 30.72 |
| MAC Pulp 5.0 L/ft² rinse | Undiluted | 46.43 | 46.43 |
| | 1:2 | 12.78 | 25.56 |
| | 1:4 | 0.93 | 3.72 |
| | 1:8 | 0.37 | 2.96 |
| | 1:16 | 0.19 | 3.04 |
| | 1:32 | <0.20* | —* |
| | 1:64 | <0.20* | —* |
| | 1:128 | <0.20* | —* |
| | 1:256 | <0.20* | —* |

*Endotoxin values below lower limit of standard endotoxin curve.

As may be seen from Table 7 and FIGS. 10 and 11, the purified cellulose gives quite good results when tested for pyrogen levels, the undiluted sample following the 5L/ft² rinse showing less than 50 pg/ml of pyrogens.

Having now fully described the invention, it will be appreciated by those with ordinary skill in the art that the same can be practiced with a wide and equivalent range of compositions and methods for forming same without affecting the spirit and scope of the invention or any embodiment thereof.

What is claimed and desired to be covered by Letters Patent is:

1. A method of substantially eliminating false positive Limulus Amebocyte Lysate ("LAL") tests for pyrogen from an effluent obtained from passing a biological liquid through a cellulose containing separation media comprising substituting for said separation media a cellulose containing separation media wherein said cellulose contains at least about 90% alpha-cellulose and is essentially free of non-specific pyrogenic reactivity as measured by the LAL tests, whereby said false positive LAL tests are substantially eliminated.

2. The method of claim 1 wherein said LAL test is the gel-clot test.

3. The method of claim 1 wherein said LAL test is the MS-2 test.

4. The method of claim 1 wherein the separation media is electropositive.

5. The method of claim 1 wherein said separation media is a filtration media.

6. The method according to claim 5 wherein said filtration media comprises a micro-porous filter sheet of uniform porosity comprising at least about 20 wt.% of fine particulate and not more than about 80 wt.%, distributed within an interfelted matrix of cellulose fibers, said cellulose fibers being prepared from a cellulose pulp mixture comprising an unrefined cellulose pulp having a Canadian Standard Freeness of from about +400 to about +800 ml., and a highly refined cellulose pulp having a Canadian Standard Freeness of from +100 to about −600 ml.

7. The method of claim 6 wherein the microporous filter sheet contains about 40-70 wt.% of fine particulate.

8. The method of claim 6 wherein said interfelted matrix of cellulose fibers comprises 80-20 wt.%.

9. The method of claim 8 wherein the ratio of said unrefined cellulose pulp to said highly refined cellulose pulp is from about 0.1:1 to about 10:1.

10. The method of claim 9 wherein said ratio is from about 0.2:1 to about 1:1.

11. The method of claim 6 further containing a charge modifier.

12. The method of claim 11 wherein said charge modifier is selected from cationic silica, melamine-formaldehyde cationic colloid, and polyamido polyamine epichlorohydrin.

13. The method of claim 12 wherein the surfaces of the fine particulate and the cellulose pulps possess a positive zeta potential.

14. The method of claim 12 wherein the charged modifier is polyamido polyamine epichlorohydrin.

15. The method of claim 6 wherein at least a portion of said fine particulate is selected from fumed silica, fumed alumina, or activated carbon.

16. The method of claim 1 wherein said separation media is a chromatographic separation media.

17. The method of claim 16 wherein the chromatographic separation media comprises a solid stationary phase substantially homogenous with respect to each component thereof, said solid stationary phase comprising a porous matrix of cellulose fiber having particulate immobilized therein, at least one of said cellulose or particulate therein having a chromatographic functionality and being effective for chromatographic separation.

18. The method of claim 17 wherein said porous matrix of cellulose fibers comprises unrefined cellulose pulp having a Canadian Standard of Freeness of from about +400 ml to about +800 ml in admixture with a highly refined cellulose pulp having a Canadian Standard of Freeness of from about +100 ml to about −600 ml.

19. The method of claim 18 wherein the ratio of said unrefined cellulose pulp to said refined cellulose pulp is from about 0.1:1 to about 10:1.

20. The method of claim 19 wherein said ratio is from about 0.2:1 to about 1:1.

21. The method of claim 19 wherein said particulate comprises about 20-80 wt.% thereof.

22. The method of claim 21 wherein said particulate comprises about 40-70 wt.% thereof.

23. The method of claim 17 wherein said solid stationary phase comprises a plurality of sheets of said solid stationary phase.

24. The method of claim 16 wherein said media is an ion-exchange media.

25. The method of claim 16 wherein said media is an affinity chromatographic media.

26. The method of claim 16 wherein said media is a reverse phase chromatographic media.

27. The method of claim 17 wherein said cellulose comprises refined and unrefined cellulose, wherein each of said refined and unrefined cellulose consists of highly purity cellulose.

28. The method of claim 17 wherein said chromatographic separation media contains a charge modifier.

29. The method of claim 28 wherein said charge modifier is selected from cationic silica, melamine formaldehyde, or polyamido-polyamine epichlorohydrin.

30. The method of claim 17 wherein at least a portion of said particulate is selected from fumed silica, fumed alumina, or activated carbon.

31. The method of claim 16 wherein said:
cellulose is covalently bonded to a synthetic polymer, said synthetic polymer made from
(a) a polymerizable compound which has a chemical group capable of direct or indirect covalent coupling to said cellulose; and
(b) one or more polymerizable compounds containing:
(i) an ionizable chemical group,
(ii) a chemical group capable of transformation to an ionizable chemical group,
(iii) a chemical group capable of causing the covalent coupling of said synthetic polymer to an affinity ligand or a biologically active molecule, or
(iv) a hydrophobic chemical group.

32. The method of claim 1 wherein said cellulose is produced by the sulphite process.

* * * * *